(12) United States Patent
Abri et al.

(10) Patent No.: US 9,597,806 B2
(45) Date of Patent: Mar. 21, 2017

(54) GRIPPING ELEMENT AND GRIPPER INPUT MODULE FOR A HAPTIC INPUT SYSTEM

(71) Applicant: Karl Storz GmbH & Co. KG, Tuttlingen (DE)

(72) Inventors: Omid Abri, Berlin (DE); Stephan Schrader, Kleinmachnow (DE); Jonas Forster, Berlin (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 571 days.

(21) Appl. No.: 14/105,666

(22) Filed: Dec. 13, 2013

(65) Prior Publication Data
US 2014/0165770 A1 Jun. 19, 2014

(30) Foreign Application Priority Data
Dec. 13, 2012 (DE) ........................ 10 2012 112 247

(51) Int. Cl.
| | |
|---|---|
| *G08B 6/00* | (2006.01) |
| *B25J 13/02* | (2006.01) |
| *G06F 3/01* | (2006.01) |
| *G06F 3/0346* | (2013.01) |
| *A61B 1/00* | (2006.01) |

(52) U.S. Cl.
CPC ............. *B25J 13/025* (2013.01); *A61B 34/30* (2016.02); *G06F 3/016* (2013.01); *G06F 3/0346* (2013.01); *A61B 1/00* (2013.01); *Y10T 74/20305* (2015.01)

(58) Field of Classification Search
CPC ..................................... A61B 1/00; B25J 1/00
See application file for complete search history.

(56) References Cited

U.S. PATENT DOCUMENTS

| | | | | |
|---|---|---|---|---|
| 5,778,885 A | * | 7/1998 | Doyama ................ | A61B 5/225 600/595 |
| 7,411,576 B2 | | 8/2008 | Massie et al. | |

(Continued)

FOREIGN PATENT DOCUMENTS

JP          H102284888 A      11/1990

OTHER PUBLICATIONS

European Search Report Application No. EP 13197254.9 Completed: Oct. 14, 2015; Mailing Date: Oct. 23, 2015 9 pages.

(Continued)

*Primary Examiner* — Shirley Lu
(74) *Attorney, Agent, or Firm* — Whitmyer IP Group LLC

(57) ABSTRACT

A gripping element for arrangement on an adapter element in order to form a gripper input module for a haptic input system for controlling an object, including a receptacle for holding at least two fingers of a user therein, wherein, at least in one portion, the receptacle has a functional connection to at least one sensor means, and at least one connection element for arranging the gripping element on the adapter element, wherein the receptacle is configured such that movement information of a movement of at least one finger of the user in the receptacle can be detected by the sensor means and hence the movement information can be transmitted for controlling the at least one object. There is also disclosed a corresponding adapter element, a gripper input module consisting of a gripping element and adapter element, and also to a haptic input system and medical instrument system.

21 Claims, 7 Drawing Sheets

(56) References Cited

U.S. PATENT DOCUMENTS

| | | |
|---|---|---|
| 7,480,600 B2 | 1/2009 | Massie et al. |
| 2004/0046732 A1 | 3/2004 | Chesters |
| 2005/0043719 A1 | 2/2005 | Sanchez et al. |
| 2008/0154246 A1 | 6/2008 | Nowlin et al. |
| 2008/0167662 A1 | 7/2008 | Kurtz |
| 2010/0225209 A1 | 9/2010 | Goldberg et al. |
| 2012/0071891 A1* | 3/2012 | Itkowitz .............. A61B 19/2203 606/130 |

OTHER PUBLICATIONS

Kawasaki, et al.; "Finger Pad Force Display for Hand Haptic Interface"; Aug. 21-24, 2010; 6 pages.

Endo, et al. "Five-Fingered Haptic Interface Robot: HIRO III" Jan.-Mar. 2011; 14 pages.

Kawasaki, et al.; "Multi-Fingered Haptic Interface Robot Handling Plural Tool Devices"; 2007; 6 pages.

* cited by examiner

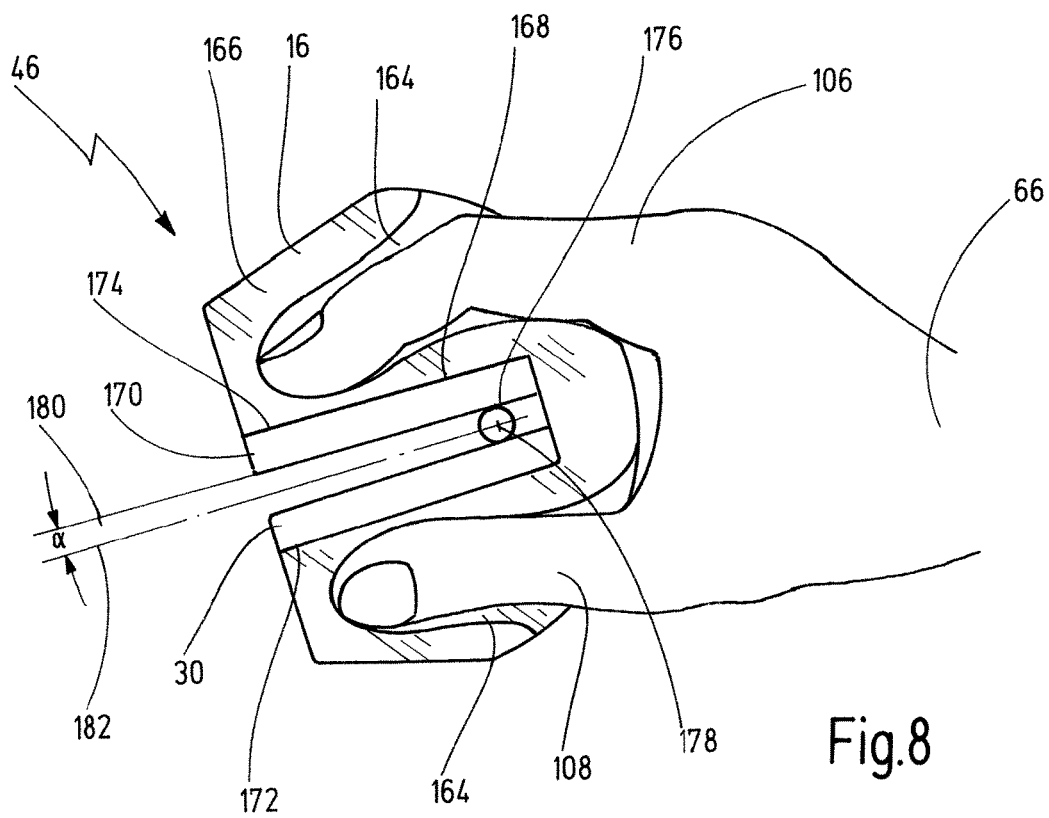

GRIPPING ELEMENT AND GRIPPER INPUT MODULE FOR A HAPTIC INPUT SYSTEM

FIELD OF THE INVENTION

The present invention relates to aspects of a gripping element for arrangement on an adapter element or an adapter element for detachably holding a gripping element, respectively in order to form a gripper input module for a haptic input system for controlling at least one object. Furthermore, the present invention relates aspects of a corresponding gripper input module, a haptic input system and a medical instrument system.

BACKGROUND OF THE INVENTION

Haptic input systems are used in the industrial and medical sector, but also in the end-user sector, in order to transmit the movement of a user, in particular of at least one hand, to another system. These other systems can be directly actuatable devices, such as e.g. medical instruments, machines, vehicles which can be controlled remotely, robots or the like. Alternatively, the information contained by the input into these haptic input systems can also be implemented in (purely) computer-related applications, such as e.g. in CAD applications or virtual reality.

These haptic input systems usually display different combinations of degrees of freedom and axes, within which a corresponding movement can take place. Here, it is usually possible to find three translational and three rotational degrees of freedom. These degrees of freedom can in each case be provided with or without force feedback. Here, force feedback means either responses from a device to be controlled or responses from a computer system, which experiences the corresponding device in reality or experiences the computer system in virtual reality and, by means thereof, transmits force feedback-type feedback to the user of the haptic input system. In addition to these aforementioned six degrees of freedom of spatial movement, even more functions on the haptic input system can furthermore be provided to the user. A gripper function is such an exemplary function.

This gripper function is an actuation of a device to be controlled (in the real world or in virtual reality), which is achieved by a gripping movement by the respective user using his hand. In this context, a gripping movement is to be understood to mean such a movement in which a user moves at least two of his fingers on one hand toward one another, wherein, in general, at least one of these at least two fingers is a thumb.

In order to detect movements of a finger of a user, U.S. Pat. No. 7,480,600 B2 describes a device in which a thimble is placed onto the fingertip of a user. By means of a suspension device, this thimble is connected to the device described there in such a way that translational movements of the fingertip in space can be detected. Furthermore, the transmission of force feedback to the respective finger has also been described. In order to be able to detect a gripping movement of a user, U.S. Pat. No. 7,480,600 B2 proposes combining a plurality of the above-described devices and therefore track e.g. three fingers of one hand in terms of their motion by means of an appropriate combination device. This means that every finger to be tracked of the corresponding hand of the user is provided with an appropriate thimble, which is then in each case connected to respectively one of the devices described therein by means of its own suspension device.

Apart from the comparatively complicated procedure of having to provide each finger individually with a thimble, the design of the combination device described in U.S. Pat. No. 7,480,600 B2 leads to a complicated system of rods being present. This system becomes ever more complicated with increasing numbers of fingers to be identified, and so structural problems may also already occur in the case of three or more fingers.

U.S. Pat. No. 7,411,576 B2 describes a haptic interface, which, in particular, is suitable for movement and hence control in accordance with the aforementioned six degrees of freedom. This haptic interface has a user interface element, which consists of a nose and a detachable user connection portion. This detachable user connection portion can have various designs and can therefore have different gripper shapes. In particular, a stylus-like shape is described. In the described shapes, provision is furthermore made for function keys on the stylus-like design, which function keys can serve for controlling the haptic input system. These function keys are configured as conventional pushbuttons, which, when required, can be pressed by a finger of the user.

Controlling a gripping movement is not provided for by U.S. Pat. No. 7,411,576 B2. The otherwise-described function keys merely serve to modify the operation of the haptic input system and are moreover arranged in such a way that ergonomic operation of the haptic input system in the aforementioned U.S. Pat. No. 7,411,576 B2, as could be desired e.g. when operating cutting tools by means of such a haptic input system, is not possible.

US 2005/0043719 A1 also describes a haptic input system with a gripper part with separate input pushbuttons. Like in U.S. Pat. No. 7,411,576 B2, these input pushbuttons can be allocated various functions.

US 2008/0154246 A1 likewise describes a system for carrying out robot-controlled surgical interventions. To this end, provision is made on a handle, which, like in U.S. Pat. No. 7,411,576 B2, substantially has a stylus-like design, for a corresponding user to press together two gripping elements arranged pivotably to one another in order to cause a correspondingly similar moving together of the gripping or cutting elements in the object to be controlled. To this end, these gripping elements are securely arranged on the handle. Furthermore, US 2008/0154246 A1 provides for a corresponding user, who actuates the gripping elements for actuating the gripping or cutting tools, which are to be controlled, to have an approximate feeling for how strongly a corresponding gripping tool or cutting tool is actuated. In US 2008/0154246 A1, this is implemented by virtue of elastic, in particular also springy, elements being provided which, for example, also have different elasticity in different portions. As a result of this, a transition from e.g. a wide opening region to a narrower opening region of a corresponding tool should be effected to the user.

Like in U.S. Pat. No. 7,411,576 B2, there is also relatively non-ergonomic gripping of the handle in this case. The gripping elements arranged on this handle are, as a result of the provision with these respectively mechanical components, furthermore disadvantageous to the extent that these elastic/mechanical components are subjected to a certain amount of wear and tear, making replacement necessary from time to time. However, as a result of the secure integration into the handle in this device, this is connected with much effort. In addition to the comparatively bad ergonomic design and the aforementioned aspects in relation to wear and tear, comparatively complicated cleaning/sterilizing is furthermore required due to the depicted embodiment of the handle if the device is to be used in the vicinity of an operation site. An application of a general sheath would not redress this in this case either, since this once again reduces the user comfort of such a device.

US 2008/0167662 A1 describes a control system for controlling a robot, in particular for surgical interventions. In this respect, the device provides various control devices, for example joysticks, in order to actuate the corresponding instrument to be controlled. In order to transmit a corresponding haptic feedback from the instrument to be controlled to the user, US 2008/0167662 A1 proposes that a corresponding user makes use of a tactile glove. This glove is configured in such a way that it contains appropriate inflatable elements, which are to transfer the respective forces to a hand of a respective user, which forces the user would also experience if he were to actuate the corresponding instrument directly. In other words, the device of US 2008/0167662 A1 offers a conventional control system with the corresponding control devices, the disadvantages of which were already mentioned above, and in this case integrates a feedback system in the form of a glove.

Even if the proposed glove offers optimization in respect of the feedback functions of such a system, the conventional input equipment furthermore remains in respect of the ergonomics and safe operability of a corresponding control system. The aforementioned disadvantages of unsafe operation, possible slippage and difficult control due to inexpedient ergonomic conditions are not removed by the use of such a tactile glove either.

Although, purely theoretically, the haptic input systems described above in an exemplary manner enable the transmission of gripper information to a target system, this is however brought about by means of e.g. a freely suspended hold of the hand and, individually for each finger, by a complicated connection of the hand to the individual haptic input systems in U.S. Pat. No. 7,480,600 B2 or by means of a more stylus-shaped arrangement in U.S. Pat. No. 7,411,576 B2 and US 2008/0154246 A1, which arrangement is likewise unsuitable for targeted controlled gripper-like movement. As a result of the comparatively non-ergonomic actuation, there can easily be slippage or shifting from the actual position in both devices, which may be fatal, particularly in difficult applications such as e.g. a surgical intervention or complicated mechanical interventions. This also applies to the system from US 2008/0167662 A1, which substantially resorts to conventional input equipment for control purposes. Moreover, the above-described devices establish the connection to the user by means of elements securely arranged on the devices, like e.g. in U.S. Pat. No. 7,480,600 B2, US 2008/0154246 A1 and US 2008/0167662 A1, or by means of elements with an at least comparatively complicated design, which are not suitable for in-depth cleaning either, like in U.S. Pat. No. 7,411,576 B2. As a result, these devices are disadvantageous for uses in the medical sector, particularly in surgical interventions in the vicinity of the operation site.

SUMMARY OF THE INVENTION

In accordance with one aspect there is provided a gripping element and a corresponding adapter element, which together form a gripper input module, which is a component of a haptic input system for controlling at least one object, which gripping element and corresponding adapter element enable ergonomic actuation of a haptic input system, particularly in respect of gripping movements, or gripper-like movements, wherein, in particular, secure control and movement should be made possible for the user in the process.

Furthermore, in accordance with another aspect, the device should preferably also be simple to clean, in particular, to be simple to sterilize at the exposed gripping and contact regions with a user.

In accordance with a first aspect there is provided a gripping element for arrangement on an adapter element in order to form a gripper input module for a haptic input system for controlling at least one object, comprising
at least one receptacle for holding at least two fingers of a user therein, wherein, at least in one portion, the receptacle has a functional connection to at least one sensor means, and
at least one connection element for arranging the gripping element on the adapter element,
wherein the receptacle is configured such that movement information of a movement of at least one finger of the user in the receptacle can be detected by the sensor means and hence the movement information can be transmitted for controlling the at least one object.

Dividing the gripper input module into a gripping element and an adapter element provides the option of configuring a corresponding haptic input system in such a way that a fixed part can be kept sterile, for example by covering with a protected sheath or constant sterilization, while an interchangeable part, namely the gripping element, can be removed for sterilization purposes, for example in an autoclave or other sterilization devices. Additionally, the gripping element can also be provided as (sterile) disposable element.

One further advantage of this refinement may be seen in the option of being able to provide a respective gripping element for a specific purpose or a specific application in medical or other control applications. Thus, the number of receptacles and/or the number of fingers per receptacle can in each case be different depending on the desired control and can be adapted by interchanging a respective gripping element. Here, the gripping element is arranged on the adapter element, e.g. in a force-fit, interlocking or cohesive manner or in any combination of these types of connection.

A fixed position for the respective fingers of a user is provided by the at least one receptacle. Here, at least one receptacle for at least two fingers should be understood to mean both a continuous region and a region interrupted by e.g. webs. A corresponding finger of a user is furthermore situated "in the receptacle" when it is arranged at the space provided for the positioning thereof. Here, this can be both simple depressions, which can hold the finger, and also, in an exemplary variant, openings in the gripping element, which have approximately the size and/or shape of the finger and surround the latter at least in part at the sides or all of the way around. A movement "in the receptacle" accordingly includes a movement of the finger within the scope of free play of the finger in this receptacle and also a deformation of the material restricting or containing the receptacle.

As a result of the fact that the corresponding finger or the corresponding fingers of a user are held in at least one receptacle, a secure hold and hence a secure and reliable operation of a corresponding haptic input system are ensured. Furthermore, detecting movements in the receptacle ensures that the user does not need to leave the region of the receptacle, i.e. the region provided to him by the receptacle, with his fingers either. This further contributes to the secure and reliable operation of the haptic input system. A movement of the finger, for example to carry out a gripping procedure, which is implemented by a gripping movement of the fingers, can therefore be realized very ergonomically. In so doing, the user for example simply reaches into the gripping element with his fingers, therefore has a secure hold on the haptic input system for the spatial control of at least one object and can then, by gripping movements, simultaneously and without loss of the secure hold on the haptic input system, trigger gripping, cutting or any other comparable actuation on the object to be controlled.

The option of detecting the associated movement information by the movement of the at least one finger of the user in the receptacle by the corresponding sensor means includes both cases in which the sensor means is present in the gripping element and cases where the sensor means is present on the adapter element or on an element with a functional connection thereto. As will still be explained in the following text, a corresponding sensor can therefore be present in either the gripping element, the adapter element or in an external device, which can also be a component of the haptic input system. The exemplary force-fit, interlocking and/or cohesive arrangement of the gripping element on the adapter element furthermore guarantees that the movements in the aforementioned at most six degrees of freedom in the haptic input system can be ensured when the user controls the haptic input system by means of the gripping element.

Incidentally, in this context, the term "movement information" means any information which can be obtained from a movement of a corresponding finger, such as e.g. direction, speed, force, pressure, position and duration. This movement information can then be transmitted directly or indirectly to the object to be controlled in order to control the latter. In so doing, "movement" includes both an actual movement, i.e. a change in the position of the respective finger or the respective fingers, and a movement which is not carried out (completely), in which, for example, a corresponding exertion of force by the respective finger or the respective fingers impinges on a rigid or only slightly changeable resistance, which therefore suppresses the actual movement. In other words, the actual movement would occur if it were not impeded by the resistance. Thus, for example, such an exertion of force can then correspondingly be detected as movement information.

In a further refinement of the gripping element, the gripping element is substantially produced from an elastic material and/or the functional connection to the at least one sensor means is realized by an elastic material.

Embodying the whole gripping element by an elastic material may firstly be advantageous in that this likewise contributes to the ergonomics of all of the equipment. The shape of the gripping element can therefore be adapted to small differences in the shapes of the hands of different users of the haptic input system. Likewise, an elastic material as gripping element has a positive contribution to the user comfort.

This refinement, like the refinement in which the functional connection to the at least one sensor means is realized by an elastic material, furthermore may provide the advantage of the user thus not having to directly grip the sensor or a general sensor means, such as a sensing device, a pressure gauge, etc. This may enable the refinement of haptic input systems which, in particular, have gripping elements with closed and also smooth surfaces, which are therefore easier to clean. Here, an appropriate sensor means can either be arranged directly under the surface of the receptacle and force transmission can be realized by an elastic material or else, for example, be arranged in the adapter element, wherein, in this case, there can also be transmission of the movement, in the form of e.g. a force transmission, into the adapter element through the elastic material and by means of the functional connection between gripping element and adapter element.

In a further refinement of the gripping element, the at least one receptacle is configured such that a movement of at least one finger of the user in the at least one receptacle can, by means of the connection element, be detected by at least one sensor means, which is arranged on the adapter element.

In this refinement, the sensor means is therefore present on the sides of the adapter element. The gripping element, for example in the form of the material forming the latter, therefore serves as functional connection between at least one finger of the user and the sensor means. This is rendered possible by the aforementioned functional connection between gripping element and adapter element.

One advantage of this refinement may be that the gripping element thus can make do without sensor means, that is to say e.g. without sensor electronics or the like. Such a gripping element can therefore be manufactured in a relatively simple and uncomplicated manner. On the one hand, this renders simple cleaning or sterilizing of the gripping element possible, since there is no risk to relatively complex or sensitive electronics by e.g. aggressive chemicals or high temperatures, as occurring in autoclaves for example. On the other hand, this thus may also enables a refinement of the gripping element as (sterile) disposable article since the production can be significantly more cost-effective and easier as a result of the lack of more complicated or complex electronics and other measuring or sensor elements, or sensor means in general, and so the use as disposable article is economical.

In a further refinement of the gripping element, the gripping element has at least one sensor means for detecting at least one movement of at least one finger of the user in the receptacle.

In this refinement, one sensor means, e.g. one sensor, is now present in the gripping element. This sensor means can now be arranged directly in the receptacle or else at another point of the gripping element that has a functional connection to the receptacle. The latter is possible, for example, due to the material of which the gripping element consists. As a result, it is possible to detect the movement of the at least one finger of the user in the receptacle and, for example, convert this into electrical signals in order ultimately to enable a control of the at least one object.

Providing the at least one sensor means in the gripping element renders it possible for the corresponding gripping element with the sensor means to be able to be replaced in a simple manner. This may be advantageous if, for example, one or more sensor means are defective and have to be replaced. In other devices, this normally means a complicated repair. However, due to this refinement, it is sufficient merely to replace the gripping element. By way of example, this may, in particular, be advantageous when the respective sensor means are comparatively simple and cost-effective sensors and other repair would be significantly more costly than the component per se. Furthermore, in such a refinement it is also feasible to provide a use for the gripping element as disposable article. However, this depends decisively on the specified use and economical aspects.

In a further refinement of the gripping element, the at least one sensor means has at least one sensor, e.g. at least one pressure sensor, one force sensor or one movement sensor.

As a result of using these types of sensors, it is possible to detect the movement of a corresponding finger in the receptacle, in particular by detecting pressure of the finger into or onto the material of the gripping element. Furthermore, in addition to pure pressure detections, it is also possible to detect tensions or movements of the material, and so, for example, it is also possible to record shearing forces. Depending on the desired field of application, this enables a very detailed detection of the movement information of the at least one finger in the receptacle.

In a further refinement of the gripping element, the at least one receptacle is furthermore configured such that it enables a transmission of at least one item of force-feedback information to at least one finger, which is held in the at least one receptacle, of the user.

The transmission of force-feedback information leads to the user receiving a haptic impression from the site of use of the object to be controlled, ideally in such a manner as if he were working directly on the object to be controlled and, as a result thereof, experiences the haptic impressions himself. In this context, "force feedback" therefore means, firstly, the haptic impressions which emerge directly from the object to be controlled, such as e.g. resistance when actuating a clamp or scissors, and also notifications transformed into such haptic feedbacks, for example if a warning or any other information, which, in particular, requires the attention of the user, should be transmitted to him. In this context, force feedback can have different implementations. Thus, for example, this can be understood to mean, firstly, actual resistances or counteracting forces during gripping and, secondly, actions generating attention, such as e.g. vibrations.

The provision of force-feedback information, or the transmission thereof to at least one finger of the user, therefore may be advantageous in that the user, firstly, can thus be made aware of different conditions on the object to be controlled itself or on the whole actuation or operation procedure. By the transmission in respect of the receptacle per se, it is furthermore possible that corresponding devices, such as e.g. actuators, do not need to come into direct contact with the user but rather effecting or transmitting by means of e.g. the material of the gripping element is also possible.

In a further refinement of the gripping element, the at least one receptacle is configured such that the at least one item of force-feedback information can, by means of the connection element, be transmitted from the adapter element to at least one finger, which is held in the at least one receptacle, of the user.

In this refinement, like in the corresponding refinement with the sensor means in the adapter element, it is possible, as already described above, to provide for any technology, like e.g. actuators in this case, in the adapter element. This means that the gripping element itself can be provided or manufactured either as a product that is easy to sterilize or even as a disposable product. This accordingly contributes to hygiene regulations, as are present e.g. in the case of surgical operations, being easy to be observed. Depending on the material used for the gripping element, there can also be a certain amount of wear and tear by the use by a user. Thus, in general, it is also possible, independently of surgical interventions, for there to be a simple and cost-effective replacement of gripping elements, and so a new gripping element can be provided on a haptic input system at regular intervals. This further increases the comfort for the user.

In a further refinement of the gripping element, the gripping element has at least one actuator, by means of which at least one item of force-feedback information can be transmitted to at least one finger which is held in the at least one receptacle, of the user.

In this refinement, the force-feedback information is therefore provided directly by the gripping element or by actuators which are arranged in the latter. Coupling to the whole system can in this case, as is also the case in the above-described sensors or sensor means, either be brought about directly on the gripping element or effected by means of the adapter element. For the latter variant, the adapter element and the gripping element would then each provide corresponding contact connection sites.

By providing the actuators in the gripping element, it is also possible in this case to carry out simple repairs if malfunctions are present. This is particularly attractive if the actuators are comparatively inexpensive components, in which complicated repair in a device to be reused would exceed the scope of the component costs. Depending on the type and costs of the actuator, use as described above as a product that is easy to sterilize or as a disposable product also comes into question here. Accordingly, actuators can be any electrical or mechanical devices which exert vibration or pressure onto the at least one finger of the user. This can either occur directly, i.e. through or from the material of the gripping element, or can be effected through the material of the gripping element. Hence, in other words, the actuators can be arranged in such a way that they come into direct contact with the at least one finger of the user or else are separated therefrom by a material of the gripping element. In the latter case, the use of an elastic material, either for the whole gripping element or for the region of the receptacle, i.e. the contact region with the at least one finger of the user, may be advantageous. In addition to the above-described electrical or mechanical devices, e.g. hollow chambers can also be provided as actuators. The volume and pressure thereof can be modified by e.g. a fluid, such as e.g. a gas or liquid. In the case of an appropriate arrangement in the gripping element, this can then lead to pressure or at least counter-pressure on the at least one finger of the user. Precisely the use of these last-mentioned actuators in the form of hollow chambers constitutes a comparatively cost-effective variant of actuators. Accordingly, such refinements would also come into question as products that are easy to sterilize or disposable products. Analogously to electrical or optionally mechanical connections of the above-described actuators, such an actuator is then attached either by means of a connection in the form of e.g. tubing directly to the gripping element for the respective actuator or effected by means of the adapter element.

In a further refinement of the gripping element, the gripping element has at least one passive force-feedback element.

In contrast to the above-described active force-feedback elements, which transmit force-feedback information to the finger of the user by external control information, for example an electrical pulse or the increase of the pressure in a cavity by a fluid, passive force-feedback elements in particular have elements which are suitable for changing the material properties thereof. According to one example, material properties may mean the elasticity or the resistance against compression. In other words, a passive force-feedback element within the comprises an element which can modify properties as a result of a control signal in such a way that said properties can be felt by a user. Specifically, a passive force-feedback element could therefore be arranged in the gripping element material by way of example such that the user presses on this force-feedback element by means of a gripping movement (or an opening movement of the hand), either directly or effected through the material of the gripping material. Now, if there is, for example, relatively large resistance when the object to be controlled is controlled, the resistance against compression or the elasticity of the passive force-feedback element can be modified in such a way that a relatively solid material is also present in this case and hence a comparable haptic impression is created for the user. Conversely, this material can be modified in terms of its elasticity or resistance to compression in such a way that a soft material is simulated when this, for example, is also present on sides of the object to be controlled. Such an application may be advantageous, for example, in the case of, in particular, gripping or cutting processes which should be controlled remotely with the aid of the haptic input system, in order to impart to the user precisely the impression of a corresponding operation or actuation site of the object to be controlled. Nonrestrictive examples of such passive force-feedback elements are electrorheological or magnetorheological fluids, which can be modified by the application of an electric field, either directly or effected by a change in a magnetic field, in accordance with the explanations made above.

According to a further aspect there is provided an adapter element for detachably holding a gripping element, in order to form a gripper input module for a haptic input system for controlling at least one object, comprising an interface for communication with the haptic input system or the at least one object, and at least one receptacle element for holding the gripping element on the adapter element, wherein the at least one receptacle element is configured such that the adapter element and a gripping element connectable thereto can be brought into functional connection by a sensor means, for detecting movement information of at least one finger of the user in a receptacle of the gripping element.

This refinement of the adapter element enables the corresponding counter piece to the above-described gripping element. In accordance with the explanations made above, the advantage in this case may be seen in the refinement in which the detection of movement information or movements of a finger of the user in a receptacle is possible and that this information can be transmitted accordingly. In the refinement of this adapter element, this transmission occurs into the adapter element by means of the receptacle element. This can accordingly be such that mechanical information, such as e.g. forces, pressure or movement, can be transmitted through a medium of the gripping element into the adapter element, or by virtue of it already being possible for the corresponding movement information to be converted into electrical or other communication signals in advance and then being able to be transported into the adapter element by means of appropriate lines. Additional potential advantages, which may emerge from holding the finger in the at least one receptacle, were already described in the previous context with the gripping element and can be transferred accordingly to this adapter element. As a result of the provided interface, there can then furthermore be communication either with the haptic input system and, effected thereby or directly, with the at least one object. Hence, it follows that information about and from the control of the object can be transmitted to the adapter element and, as a consequence thereof, also to the gripping element. Here, too, the gripping element may be arranged on the adapter element in a force-fit, interlocking or cohesive manner or in any combination of these types of connection.

In one refinement of the adapter element, the adapter element has at least one sensor means for detecting at least one movement of at least one finger of the user.

In accordance with this refinement, the adapter element itself provides a sensor means. In this context, "sensor means" means that an appropriate sensor is either arranged directly in the adapter element or at least has a functional connection to the adapter element. By way of example, a pressure difference can be relayed to an external sensor by transmitting a fluid, without the sensor itself needing to be present in the adapter element. However, this is also understood as belonging to the refinement described above and can, in this respect, also be transmitted to the gripping element. The provision of these sensor means, e.g. the provision of the sensors in the adapter element, or having a functional connection thereto, leads to the above-described option of providing the gripping element as a product that is easy to sterilize or as a disposable product. Moreover, this refinement in general enables the simple and cost-effective replacement of the gripping element, which furthermore also contributes to the user comfort in view of possible wear and tear of the gripping element.

In a further refinement of the adapter element, the at least one sensor means has at least one sensor, e.g. one pressure sensor, one force sensor or one movement sensor.

The refinement with these sensors renders it possible to record both compressive and tensile forces, which are generated within the receptacle by the finger of the user, and also shearing forces, which can occur by possible twisting movement of the finger of the user. To this end, the material of the gripping element accordingly establishes a functional connection to the at least one finger of the user such that the corresponding tensile, compressive or shearing forces can be transmitted to the corresponding sensors in the adapter element or by means of the adapter element.

In a further refinement of the adapter element, the receptacle element is configured such that at least one item of force-feedback information can, by means of the gripping element, be transmitted to at least one finger of the user, which is held in a receptacle of the gripping element.

This refinement enables, in accordance with the above-described parallel refinement for the gripping element, that force-feedback information for example from the haptic input system or from the object to be controlled, can be transmitted to a finger. Here, this includes both refinements in which a corresponding force feedback-generating device is present in the adapter element and also refinements in which a corresponding force feedback-generating device is present in the gripping element. To this end, the receptacle element of the adapter element and the corresponding connection element of the gripping element are embodied such that it is possible for both the information with respect to forces to be transmitted directly by functional connection, i.e. by a force-fit, interlocking and/or cohesive connection, and also for electrical or else mechanical signals, such as e.g. pressure differences in a fluid, to be able to be transmitted. As a result, in accordance with the explanations made above in respect of the gripping element, this provides the option for the user to obtain force-feedback information and hence to be able to obtain a better haptic impression of the object to be controlled and the surroundings thereof. It is likewise possible to transmit warning information or other notification information to the user by means of such a force-feedback system.

In a further refinement of the adapter element, the adapter element has at least one actuator, by means of which at least one item of force-feedback information can be transmitted to at least one finger of the user, which is held in a receptacle of the gripping element.

In this refinement, an actuator is accordingly provided for in the adapter element. In accordance with the explanations made above with respect to the gripping element, such an actuator can be an actuator operated mechanically or electrically, or else, for example, a cavity with a changeable volume. The provision of the actuator in the adapter element may be, accordingly, advantageous in that the gripping element is thus kept as simple as possible and comes into question for sterilization, as a disposable product or, in general, for regular replacement. The force or movement or general change, which the actuator has during the operation thereof, is then transmitted directly to the finger of the user, either through the material of the gripping element or by suitable connections in this gripping element. As a result of this, the aforementioned functional connection is likewise established. Otherwise, further advantages may emerge from the explanations made above within the scope of the corresponding refinement for the gripping element.

In a further refinement of the adapter element, the adapter element has at least one passive force-feedback element.

As likewise already described above for the gripping element, the passive force-feedback element enables the inclusion of better haptic impressions for a user of the haptic input system. Hence, a transmission of the local conditions at the object to be controlled to the haptic input system, in particular to the gripper input module and hence to the at least one finger of the user, is possible. Further advantages and explanations may likewise emerge from the context of the corresponding refinements in conjunction with the gripping element.

In accordance with a further aspect there is provided aforementioned object is furthermore achieved by a gripper input module comprising a gripping element and an adapter element for holding the gripping element for operating a haptic input system for controlling at least one object, wherein the adapter element has an interface for communication with the haptic input system or the at least one object, and at least one receptacle element for holding the gripping element on the adapter element and wherein either the gripping element and/or the adapter element has a functional connection to a sensor means.

This refinement of a gripper input module according transfers the aforementioned refinement variants of the gripping elements and the associated potential advantages to such a gripper input module. In an exemplary refinement, the gripping element and/or the adapter element have/has the sensor means. Furthermore, in so doing, the gripping element is also arranged on the adapter element may have a force-fit, interlocking or cohesive manner or in any combination of these connection types.

In one refinement of the gripper input module, the adapter element is an adapter element according to the present disclosure.

This refinement of the gripper input module according now furthermore transfers the above-described refinements of the adapter element and the potential advantage connected therewith to a corresponding gripper input module.

In accordance with a further aspect there is provided a haptic input system for controlling at least one object, comprising an adapter element.

This refinement of the haptic input system comprising an adapter element transfers the above-described refinement variants and the respective potential advantages of the adapter element connected therewith to a haptic input system. This is then accordingly available for use with the aid of gripping elements, for example in accordance with the present disclosure.

In accordance with a further aspect there is provided a haptic input system for controlling at least one object, comprising a gripper input module of the present disclosure.

This refinement accordingly also transfers the above-described refinement variants and the potential advantages of the gripper input module connected therewith to a haptic input system. This means that the potential advantages of the gripping element according to the disclosure, optionally in combination with the adapter element according to the disclosure, are accordingly transferred to such a haptic input system, together with the refinement variants thereof.

In accordance with a further aspect there is provided a medical instrument system, having
 at least one medical instrument and
 at least one haptic input system of the present disclosure,
 wherein the at least one medical instrument can be controlled by the haptic input system.

This refinement of a medical instrument system now likewise offers the explanations made above for the haptic input system, the gripper input module connected therewith, the gripping element and also the adapter element in the respective refinement variants with the potential advantages connected therewith. Such a medical instrument system therefore serves for the operation on the patient by a user, i.e. an operating surgeon, either in the vicinity of the actual operation region or else in a remote-controlled application. That is to say that such a medical instrument system in such an application is distributed to different locations, wherein the medical instrument is situated at the location of the actual operation, i.e. at the patient, while the haptic input system is localized at the location of the operating surgeon. As a result, emergency interventions or interventions by specialists are made possible, without the latter possibly having to endure long-distance travel with the accompanying stress and tiring. In general, such a medical instrument system may also offer the potential advantage of being able to set a haptic input system in such a way that an appropriate movement ratio between the movement of the hand of the user, i.e. of the operating surgeon, and the actual movement of the object is present such that micro-interventions can also be undertaken. The corresponding movements of the operating surgeon are then for example converted true to scale, i.e. reduced. Using the gripping elements, adapter elements or gripper input modules according to the disclosure and the haptic input system, may result in the potential advantage that, in the case of the application of gripping movements by a user, as can be undertaken e.g. for an actual gripping with a clamp, a cutting or similar movement, in particular, ideal haptic feedback can be made available to the operating surgeon, i.e. to the user of the haptic input system. Ultimately, this also improves the overall result of the operation and therefore also contributes to improving the chances of success and the recovery of the patient.

It is understood that the features mentioned above and the features yet to be explained below can be used not only in the respectively specified combination, but also in other combinations or on their own, without departing from the scope and spirit of the present invention.

BRIEF DESCRIPTION OF THE DRAWINGS

Some aspects will be described and explained in more detail below on the base of a few selected exemplary embodiments, in conjunction with the attached drawings. In detail:

FIG. 8 shows a further exemplary embodiment of a gripping element and adapter element in accordance with one aspect, FIG. 9 shows a further exemplary embodiment of a gripping element in accordance with one aspect, comprising a force-feedback system.

DETAILED DESCRIPTION OF THE INVENTION

Figure 1:
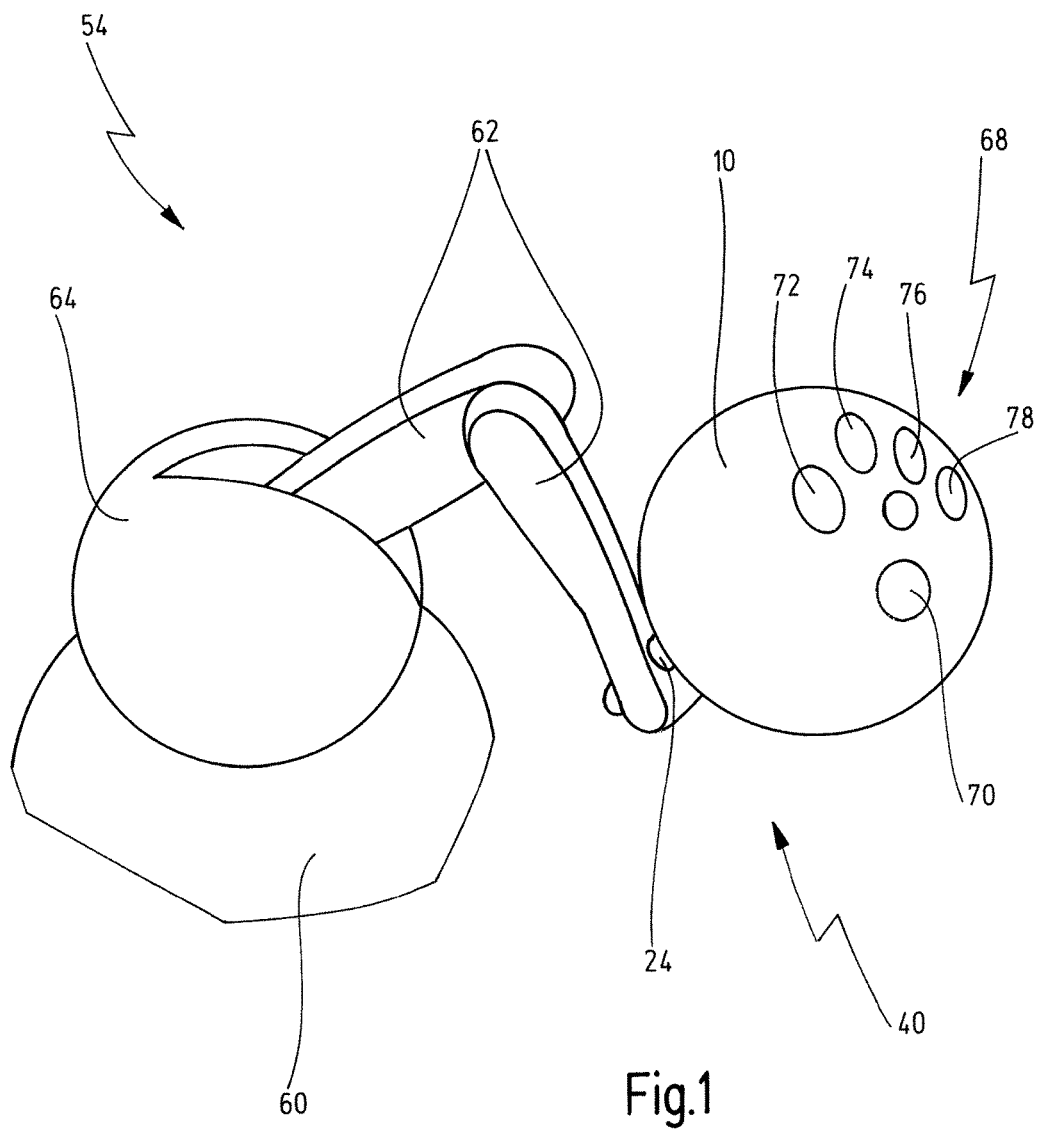
FIG. 1 shows a schematic perspective illustration of a gripper input module, comprising gripping element and adapter element, in accordance with one aspect, arranged on a haptic input system.

A gripping element according to one aspect is shown and described in conjunction with FIGS. 1, 2 and 4 to 11 and is respectively denoted by reference signs 10, 12, 14, 16, 18 and 20 in its entirety. An adapter element according to one aspect is shown and described in conjunction with FIGS. 1, 3, 4 to 8 and 11 and is respectively denoted by reference signs 24, 26, 28, 30 and 32 in its entirety. A gripper input module according to one aspect is shown in more detail and described in conjunction with FIGS. 1, 4 to 8 and 11 and is respectively denoted by reference signs 40, 42, 44, 46 and 48 in its entirety. A haptic input system according to one aspect is shown and described in more detail in conjunction with FIGS. 1, 4 and 12 and is denoted by reference sign 54 in its entirety. A medical instrument system according to one aspect is shown in more detail and described in conjunction with FIG. 12 and is denoted by reference sign 58 in its entirety.

A haptic input system 54, comprising its individual components, the gripper input module 40 and a base 60, is shown in conjunction with FIGS. 1 to 5. The gripper input module 40 is arranged on the base 60 by means of an arrangement 62. This arrangement 62 and the rotatable arrangement of an attachment 64 on the base 60 render it possible for the gripper input module 40 to be able to be moved in six degrees of freedom. These six degrees of freedom are composed from three translational and three rotational degrees of freedom. Hence, as indicated in an exemplary fashion in FIGS. 4 and 5, the gripper input module can be moved to any position in relation to the base 60 by a hand 66 of a user. In other words, the gripper input module 40 accordingly follows the movements of the hand 66, merely restricted by the embodiment in length and rotatability of the base 60 with arrangement 62 and attachment 64.

The gripper input module 40 has the gripping element 10, which is arranged on the adapter element 24. To this end, the adapter element 24 is arranged on the base 60 by means of the arrangement 62. Accordingly, this arrangement may be a force-fit, interlocking and/or cohesive type, such that a movement of the adapter element 24 is transmitted to corresponding movements of the arrangement 62 and of the attachment 64. The gripping element 10 is likewise connected to the adapter element 24. As a result, a user, who comes into contact with the whole haptic input system 54 by means of the gripping element 10, can initiate the corresponding above-described movements in the six degrees of freedom.

So that a user (not shown) comes into contact with the haptic input system 54, the gripping element 10 has a receptacle 68. In this exemplary embodiment, this receptacle 68 in turn has five holes 70, 72, 74, 76 and 78. The respective fingers of a hand 66 of the user can be held in these holes 70, 72, 74, 76, 78. As a result, the user can grip the gripping element 10 ergonomically with his hand 66 and therefore carry out the corresponding above-described movements. Hence the gripping element 10 has an ergonomic shape. Although the receptacle 68 in this case is subdivided into individual holes 70 to 78, it is by all means feasible to subdivide a corresponding receptacle 68 into one, two, three or four openings in each case, which can then respectively hold the whole hand 66, or else only individual fingers. This can ultimately lead to an almost rotationally symmetric embodiment of the receptacle 68 in the gripping element 10 in relation to a longitudinal axis 80 of the adapter element 24. As a result, a corresponding user would be unconstrained as to how he introduces his hand 66 into the receptacle 68 of the gripping element 10. In order to prevent shifting of the fingers of the hand 66, the receptacle 68 can then additionally have at least individual depressions, in which the respective fingers are held. Overall, the exemplary receptacle 68 is embodied such that it has a thickening 84 at a proximal end 82 in all variants. This thickening 84 ensures that the hand is held ergonomically by virtue of the palm of the hand 86 being able to rest on this thickening 84. In the sectional illustrations depicted in the following, the receptacle 68, or equivalents thereof in the following exemplary embodiments, is, in accordance with the above-described embodiment variants, in each case depicted as one receptacle. However, this does not preclude the subdivision into individual portions, as depicted in e.g. FIG. 1.

Figure 2:
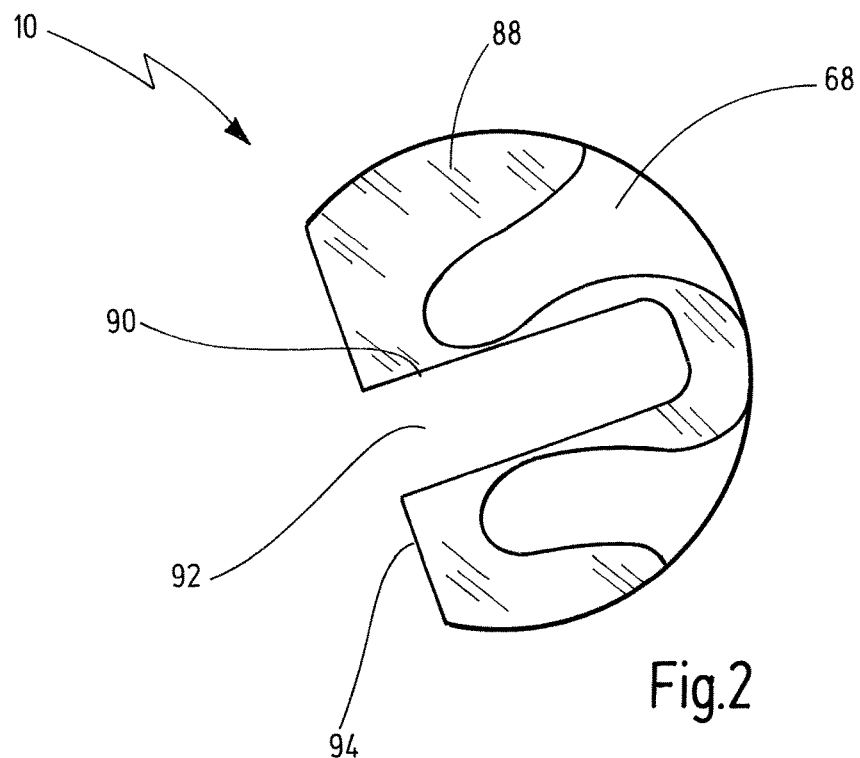
FIG. 2 shows a schematic sectional illustration of a gripping element, in accordance with one aspect.

FIG. 2 shows an individual depiction of a gripping element 10 according to one aspect. This gripping element 10 has the corresponding receptacle 68 and also a body 88. In the present exemplary embodiment, this body 88 has a spherical design. This sphere-like design furthermore contributes to the ergonomics during use of the gripping element 10 by a hand 66 of the user. A connection element 90 in the form of an opening 92 is furthermore situated in the body 88 of the gripping element 10. This connection element 90 serves for the force-fit arrangement of the gripping element 10 on the adapter element 24, as will still be explained in more detail below. In addition to the opening 92, the connection element 90 also has a resting edge 94.

Figure 3:
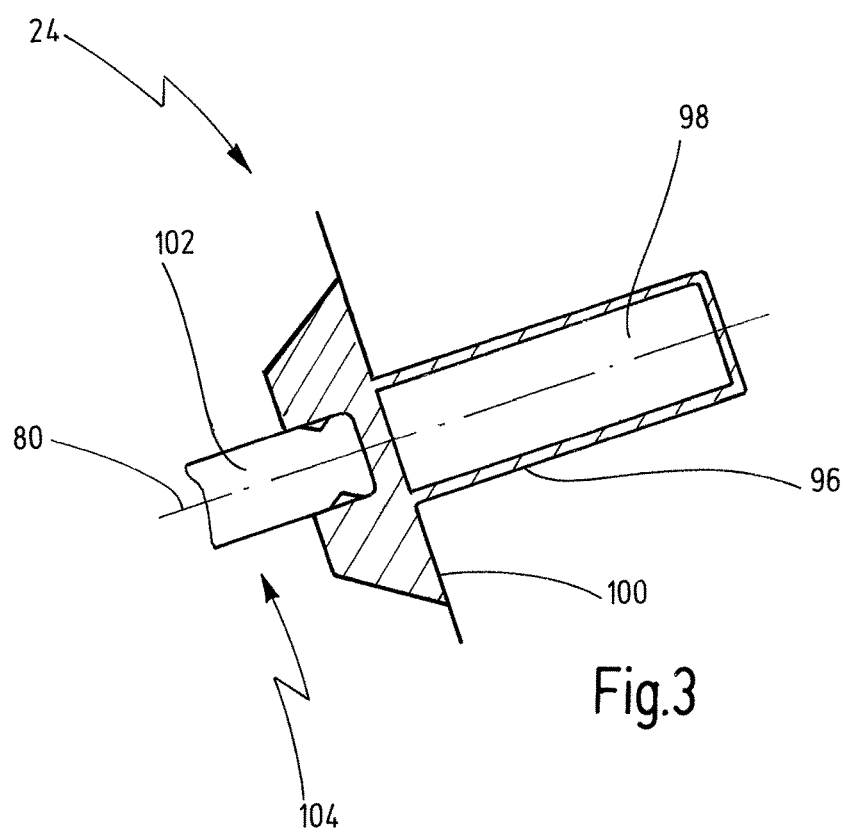
FIG. 3 shows a schematic sectional illustration of an adapter element in accordance with one aspect.

FIG. 3 shows the adapter element 24. The adapter element 24 has a receptacle element 96 in the form of a rod-shaped element 98, and a resting area 100. This rod-shaped element 98 is inserted into the opening 92 of a gripping element 10 or the gripping element 10, with the opening 92 thereof, is pushed onto this rod-shaped element 98. After the completed insertion or placement of the gripping element 10 onto the adapter element 24, the resting edge 94 comes to rest on the resting area 100. As a result, connection element 90 and receptacle element 96 are connected to one another. In other words, there therefore is a connection between gripping element 10 and adapter element 24. This connection between gripping element 10 and adapter element 24 is then of a force-fit type, for example by selection of materials with comparatively high friction with respect to one another. Thus, the material of the body 88 of the gripping element 10 can, for example, be an elastic material such as e.g. silicone, which leads to high friction on a base such as a polymer or metal for the adapter element 24. This can prevent a rotation of the gripping element 10 from occurring about the longitudinal axis 80 of the adapter element 24. Further options for preventing such a rotation would lie in an interlocking connection, for example by the provision of a tongue and groove arrangement or additional attachment elements such as pins or the like, just to name a few examples.

The adapter element 24 furthermore has a connection 102, by means of which the adapter element 24, and hence also the gripper input module 40, can be arranged on a haptic input system 54. In the present example, this connection 102 serves as interface 104 to the haptic input system 54. By means of this interface 104, there can accordingly be communication with the haptic input system. Here, "communication" firstly means the option of achieving a corresponding registration of the movement in the haptic input system 54 by the movement of the gripper input module, i.e. of the adapter element 24. Furthermore, "communication" also includes the interchange of further measurement data and other information, which can, for example, be made possible by any communication channels, such as e.g. electrical lines, fluid lines, etc. In conjunction with the example of the present gripper input module 40, such further communications are not shown in any more detail, but will still be explained in more detail in conjunction with the following exemplary embodiments and can readily be transferred to the present exemplary embodiment.

Figure 4:
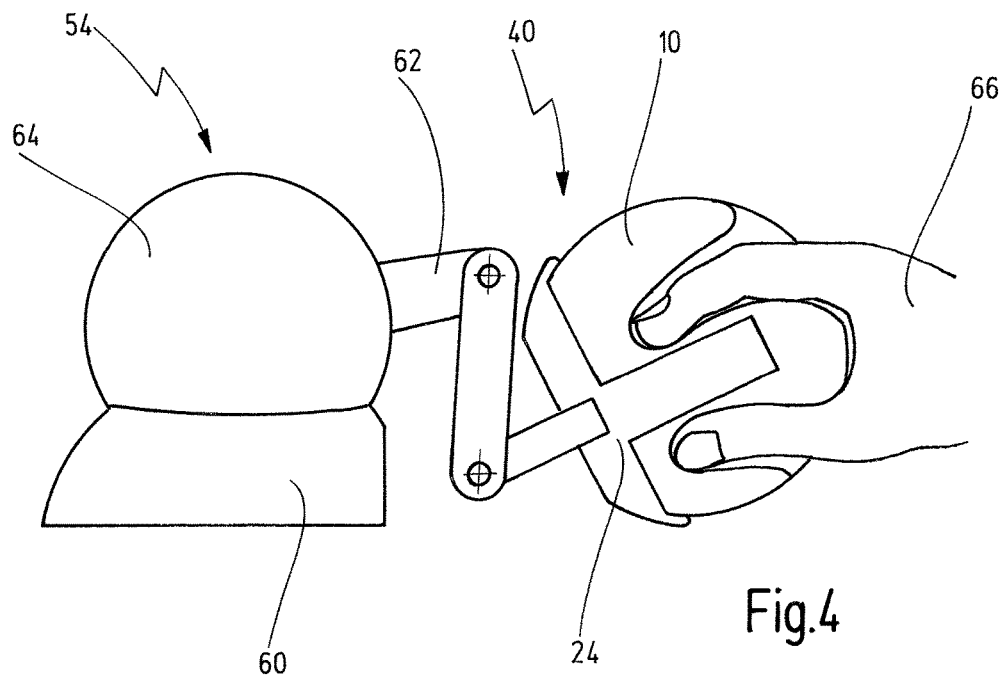
FIG. 4 shows a schematic sectional illustration of the haptic input system from FIG. 1, comprising a gripper input module in accordance with one aspect.
Figure 5:
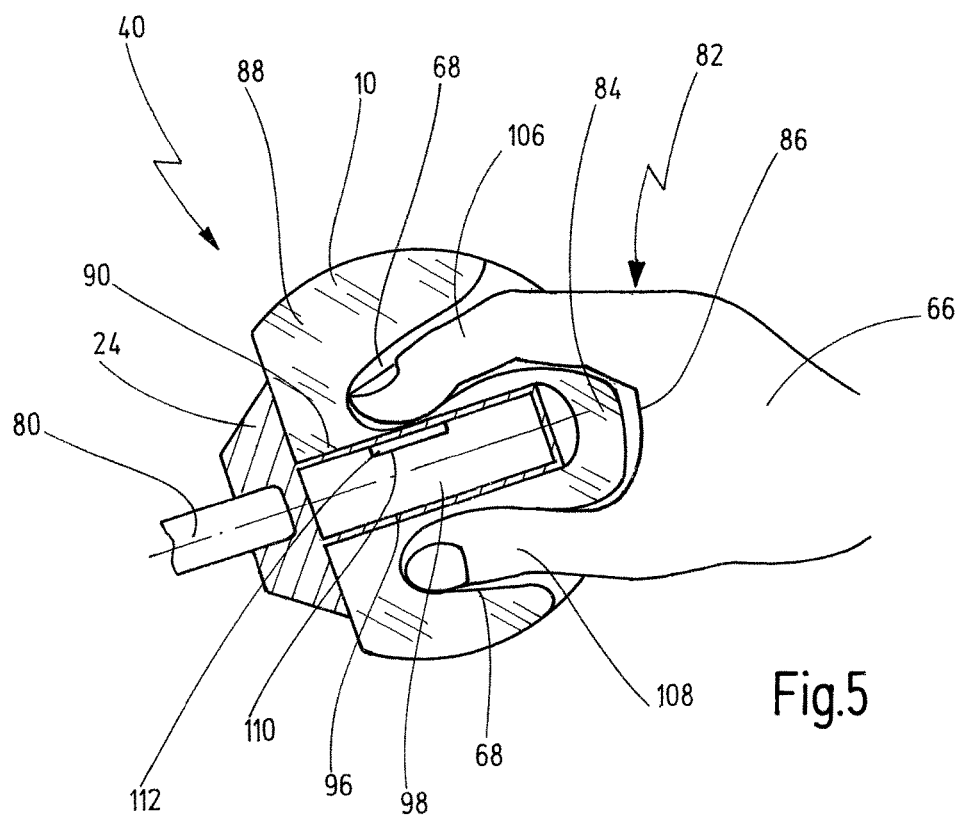
FIG. 5 shows a schematic sectional illustration of a gripping element and adapter element in accordance with an exemplary embodiment.

FIGS. 4 and 5 show, in an exemplary manner in the schematic illustrations, the reception of a hand 66 in the gripping element 10 of a haptic input system 54 or of a gripper input module 40. Here, the hand 66 comes to rest in the receptacle 68 with its fingers. For ergonomic use, resting the palm of the hand 86 on the thickening 84, which was already mentioned above, may be advantageous. As can easily be seen, in particular in conjunction with FIG. 5, fingers 106 and 108, depicted in an exemplary manner, of the hand 66 of a user extend such that they run toward one another to a greater or lesser extent in the distal direction. In other words, in exemplary embodiments, a respective gripping element, in this case the gripping element 10, is embodied in such a way that it can be gripped by the user with his hand 66 in such a way that corresponding fingers 106, 108 are arranged in a gripping hold to one another.

In this embodiment, the material of the body 88 of the gripping element 10 is arranged in such a way that material of the body 88 is likewise situated between the adapter element 24 and the fingers 106 and 108 of the hand 66. In other words, each finger 106, 108 is separated from the adapter element 24 by the body 88. Furthermore, in this exemplary embodiment, each finger 106, 108 is also completely surrounded by the body 88 or the material thereof from above and below. As already indicated previously, the material 88 in the present exemplary embodiment may be made of an elastic material. The respective fingers 106 and 108 are therefore not held rigidly in the receptacle 68 but can, in accordance with the flexibility of the body 88, carry out at least small movements. With respect to the illustration in FIG. 5, these movements for example lead upward or downward. With respect to the adapter element 24 and the receptacle element 96 thereof, this corresponds to corresponding compressive and pulling movements. Here, a compressive movement should be understood to mean such a movement in which a user substantially carries out a gripping movement with his hand 66. Such a gripping movement can, inter alia, be characterized in such a way that corresponding fingers, here e.g. the fingers 106 and 108, are arbitrarily moved toward one another. This can occur by movement of the finger 106, of the finger 108 or of both fingers. Accordingly, a pulling movement means an opening movement which counters a gripping movement. This means that such an opening movement results in the fingers 106, 108 moving apart, which, for example, can likewise be achieved by moving the finger 106, the finger 108, or by moving both fingers 106 and 108. Accordingly, as a result of the aforementioned gripping movement, pressure is exerted on the adapter element 24, in particular on the rod-shaped element 98 of the receptacle element 96. This pressure is effected by the elastic material of the body 88 of the gripping element 10.

If, as indicated in an exemplary manner in FIG. 5, a sensor means 110 in the form of a sensor 112 is now arranged on the adapter element 24 in such a way that it can register this corresponding pressure, this leads to a change in the detection signal of such a sensor 112. To this end, the sensor 112 can be e.g. a pressure sensor or a force sensor, which can register the corresponding changes in the pressure or the exerted force by the finger 106 of the hand 66. By embodying the receptacle 68 with an elastic material, at least in the region toward a sensor means 110, it is therefore possible to enable the detection of the movement or the movement information in the form of the aforementioned exemplary gripping movement by the sensor means. The information in respect of this movement obtained thereby can then be forwarded accordingly and can be used to control a corresponding object, which is to be controlled by the haptic input system 54.

Furthermore, the embodiment by the receptacle element 96 of the adapter element 24 is such that it, effected in this example by the gripping element 10, can be clasped by the fingers 106, 108 such that this detection of the movement or the movement information by the sensor means 110 is likewise made possible, ultimately due to a functional connection which exists as a result of the force transmission from the finger 106 to the adapter element 24.

Within the gripping element 10, the user can also carry out corresponding pulling movements, i.e. opening movements of his hand 66, which can likewise be detected. To this end, e.g. an arrangement of the gripping element 10 on the adapter element 24 can be brought about by a cohesive and/or interlocking mechanical connection. An example of such an interlocking mechanical connection lies in, for example, the provision of at least one T-slot in one of the two elements, i.e. in the gripping element 10 or the adapter element 24, and a corresponding tongue element on the opposite element. Hence, a pulling movement would likewise be able to be transmitted to the sensor 112, i.e. the sensor means 110, and could, for example, lead to a reduction in the pressure or to a counteracting force, which can be detected. Corresponding embodiments are possible in an analogous manner for detecting shearing forces as well. A cohesive connection can be achieved by e.g. adhesively bonding the two elements, i.e. gripping element 10 and adapter element 24.

Nonrestrictive examples for the sensor 112 and also for all sensors described in the following text are (resistive) film pressure sensors, piezoelectric elements, strain gauges (SG), pressure-dependent or force-dependent capacitors, travel encoders, etc.

Figure 6:
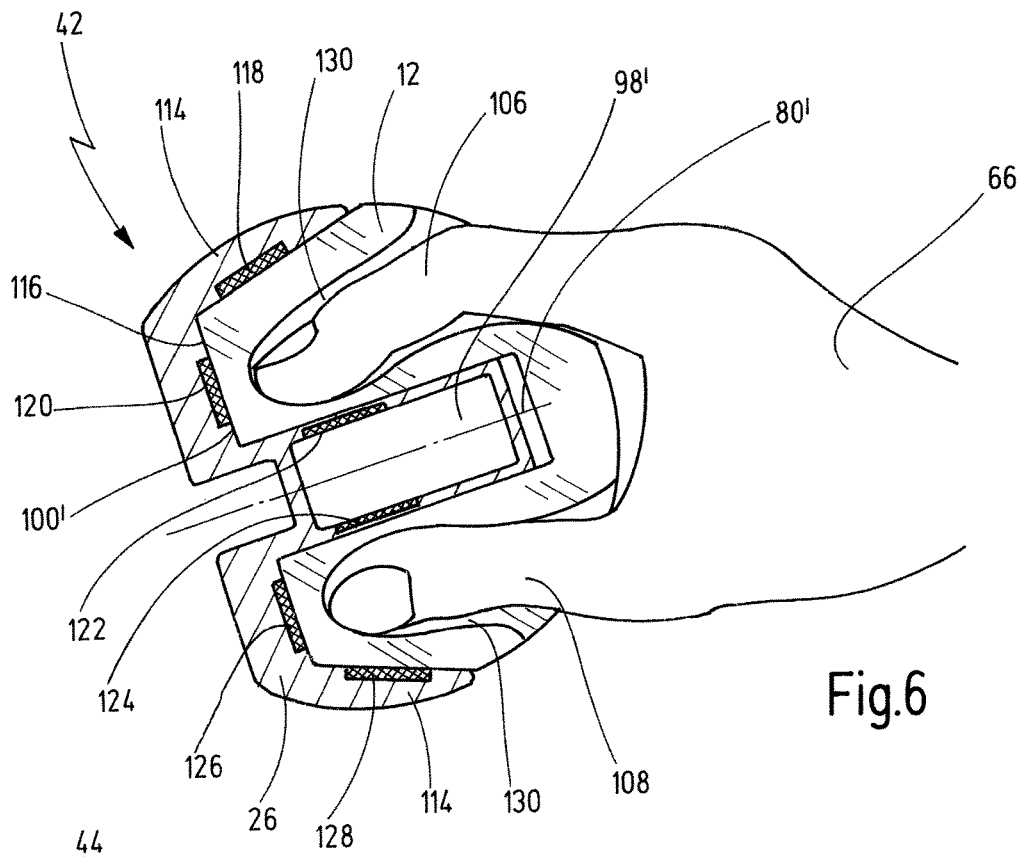
FIG. 6 shows a further exemplary embodiment of a gripping element and an adapter element in accordance with one aspect, comprising sensors in the adapter element.

FIG. 6 shows a further embodiment of a gripper input module 42. This gripper input module 42 has the gripping element 12, which is held on the adapter element 26. The adapter element 26 substantially has the same design as the adapter element 24. Hence, similar or identical components have been provided with the same reference sign, merely distinguished by means of an apostrophe. In contrast to the adapter element 24, the adapter element 26 furthermore has a side receptacle 114, which is a component of a receptacle element 116. The receptacle element 116 furthermore has a resting area 100' and a rod-shaped element 98'. The gripping element 12 likewise substantially has the same design as the gripping element 10 and is merely adapted to the slightly modified form or embodiment of the adapter element 26.

The adapter element 26 likewise has sensor means in the form of sensors 118, 120, 122, 124, 126 and 128. These sensors are respectively arranged in such a way that, firstly, the sensors 118, 120 and 122 substantially surround the finger 106 and the sensors 124, 126 and 128 substantially surround the finger 108. Since the material of the gripping element 12, at least in the region between the respective finger 106 or 108 and the corresponding sensors 118 to 128, also consists of an elastic material, a movement of a respective finger 106 or 108 within a receptacle 130 of the gripping element 12 also in this case leads to this movement or the corresponding movement information being able to be detected by such a sensor 118 to 128. In a manner comparable to the explanation made above, this is achieved by virtue of the fact that the elasticity of the material of the gripping element 12, at least in the aforementioned regions, brings about, in the form of pressure or force differences or movements, a transmission of the respective movement of the finger 106 or 108 to the sensors 118 to 128.

Thus, for example, in an exemplary embodiment where the sensors 122 and 124 are available as pressure sensors, a gripping movement by the fingers 106 and 108 can lead to the corresponding material of the gripping element 12, which is arranged between the respective finger 106 or 108 and the corresponding sensor 122 or 124, being compressed, which leads to an increase in the pressure or a transmission of this pressure to the respective sensor 122 or 124. The sensor can now register or detect this pressure change and, by means of electronics of the haptic input system not explained in any more detail here, convert this into e.g. a gripping movement with forceps, which should be controlled by the haptic input system.

Analogously, the sensors 118 and 128 can detect an opening movement by virtue of the material of the gripping element 12 in this case being compressed between the finger 106 and the sensor 118 or between the finger 108 and the sensor 128, or by virtue of a force being exerted thereon. This can then be registered by corresponding pressure or force sensors 118, 128 and, analogously to the exemplary explanation made above, lead to an opening of corresponding forceps to be controlled.

The further provided sensors 120 and 126 can likewise contribute to a detection of these gripping or opening movements, or any other possible movement of the fingers 106 and 108, and therefore increase the accuracy of the detection. In another exemplary embodiment, the sensors 120 and 126 can be embodied as movement sensors which, in general, can detect a movement of the fingers 106, 108, for example if these change from the depicted position by rotation, which should, in particular, be understood in relation to a longitudinal axis 80' of the adapter element 26. This, in particular, comes into question if the gripping element 12 is such a gripping element that has no separation of the receptacle 130 into the respective fingers of the hand 66 but rather enables a free rotation of the fingers of the hand 66 in the receptacle 130 about this axis 80'.

In general, the sensor system can therefore be arranged both perpendicular to the fingers, like, for example, the sensors 118 and 122 in relation to the finger 106, and also tangential thereto, like, for example, the sensor 120 with respect to the finger 106. Here, in this case, the specifications "perpendicular" and "tangential" are to be understood in relation to a gripping or opening movement of the fingers 106 and 108, i.e. as movements substantially upward or downward in relation to the illustration in FIG. 6. Hence, "perpendicular" in this case denotes the arrangement in which e.g. the finger 106 moves toward or away from the sensors 118 and 122, while "tangential" means the sensor 120 being passed by the finger 106 during the movement of the latter.

Figure 7:
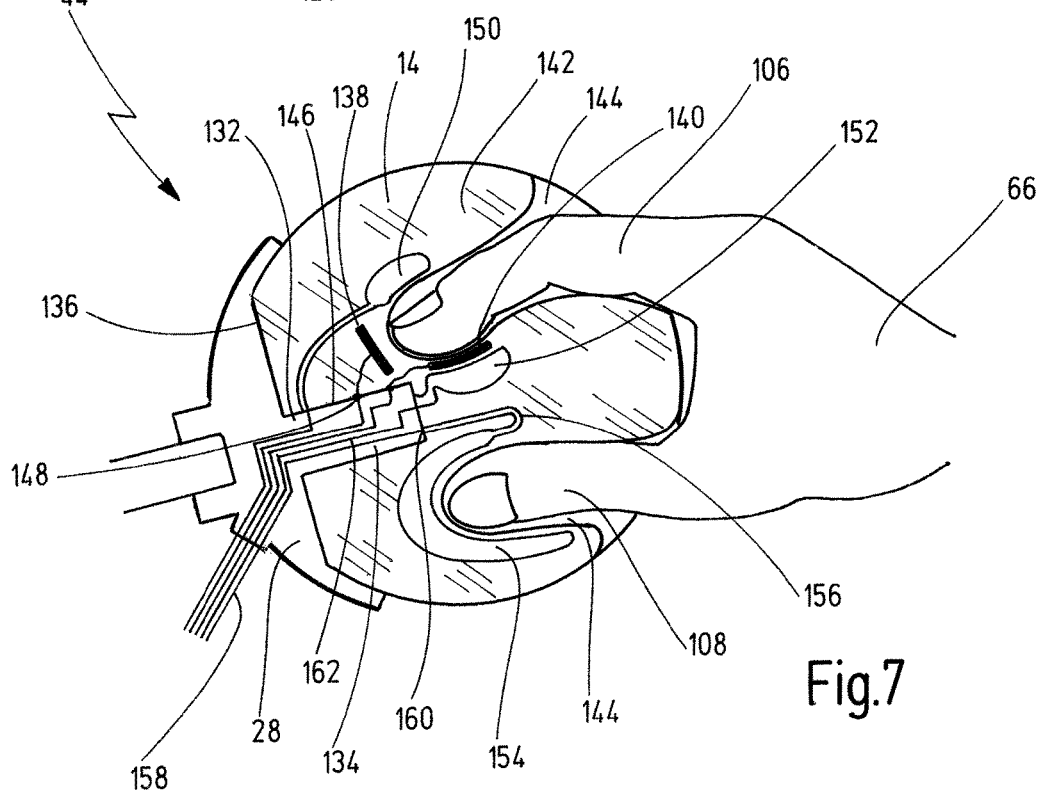
FIG. 7 shows a further exemplary embodiment of gripping element and adapter element in accordance with one aspect, comprising sensors and actuators in the gripping element.

FIG. 7 shows a further alternative embodiment in the form of the gripper input module 44. This gripper input module 44 has an adapter element 28 and a gripping element 14. The adapter element 28 likewise has a receptacle element 132. The receptacle element 132 in turn likewise has a rod-shaped element 134 and a resting area 136. In contrast to the above-described exemplary embodiments of the adapter elements 24 and 26, the adapter element 28 does not have a sensor means.

By contrast, in this exemplary embodiment of the gripper input module 44, sensor means in the form of the sensors 138 and 140 are provided in a body 142 of the gripping element 14. Analogously to the above description made in conjunction with FIG. 6, these sensors 138 and 140 are arranged either perpendicular, like the sensor 140, or tangential, like the sensor 138, to the finger 106 of the hand 66. Likewise, like in the gripper input module 42 from FIG. 6, the corresponding movement of the finger 106 can be detected in the gripper input module 44 in FIG. 7. To this end, a corresponding force or pressure is also transmitted through the material of the body 142 of the gripping element 14 to the sensors 140 or 138. This may be made possible by the use of an elastic material for the gripping element 14, at least in the region of a receptacle 144 of the gripping element 14. In contrast to the embodiment of the gripper input module 42, the sensors 138 and 140 are, as stated previously, presently arranged in the gripping element 14 in the gripper input module 44. In order to enable a corresponding functional connection and hence a transmission of movement information from the gripping element 14 to, ultimately, the haptic input system or the object to be controlled, the gripping element 14 is presently provided with a connection element 146. This connection element 146 ensures a connection to the receptacle element 132 of the adapter element 28. Here, this connection likewise once again leads to an at least force fit-type arrangement of the gripping element 14 on the adapter element 28. Additionally, or else alternatively, interlocking and/or cohesive arrangements are once again also feasible in this case. Furthermore, the connection element 146 has connection sites 148, which serve to transmit signals transmitted by the sensors 138 and 140 to a specific target system, such as e.g. an object to be controlled, by means of the adapter element 28. At these connection sites 148, a corresponding connection from the gripping element 14 to the adapter element 28, i.e., in particular, from the connection element 146 to the receptacle element 132 is made possible for these sensors 138 and 140. By way of example, such a connection can be realized by appropriate metal contacts on both sides, which, in the case of an interaction between gripping element 14 and adapter element 28, are able to establish a desired contact.

In addition to the sensors 138 and 140, the gripping element 14 furthermore has actuators 150, 152 and 154. These actuators 150, 152 and 154 in the present exemplary embodiment of the gripping element 14 or of the gripper input module 44 serve to transmit force-feedback information, or, in general, force feedback, to the fingers 106 and 108 of the hand 66 of a user. To this end, the presently shown exemplary actuators 150, 152 and 154 are embodied as stretchable cavities, for example as balloons. A fluid, such as e.g. a gas such as nitrogen or ambient air or a liquid such as e.g. water or an oil, can be pumped into these cavities. This fluid then increases the volume of the respective actuator 150, 152, 154 or said volume is reduced when the fluid is removed. This is once again made possible by the elastic design of the body 142 of the gripping element 14.

A corresponding increase in the respective volume of an actuator 150, 152, 154 by fluid flowing in or being pumped in then leads to a displacement of the material of the body 142 or of the gripping element 14, which surrounds the actuator 150, 152, 154. In relation to e.g. the actuator 150, this means that a displacement of the material of the gripping element 14 surrounding the actuator 150 occurs by the expansion of the latter. This displacement of the material ultimately has an effect on the receptacle 144 in the region of the finger 106. Subsequently this leads to pressure by the gripping element 14 in the region of the receptacle 144 occurring on the finger 106 as a result of the actuator 150 expanding. A corresponding statement can also be applied to the actuator 152. The actuators 150 and 152 are arranged in the gripping element 14 in such a way that, in each case with respect to the finger 106 as well, they are arranged above and below the receptacle 144. This therefore enables a transmission of force-feedback information from either both sides simultaneously or in each case from only the upper or lower side in relation to the finger 106. As a result, in addition to the general option of transmitting force feedback or force-feedback information to the user, there is additionally the option of transmitting the force feedback depending on the object to be controlled. By way of example, if a resistance is situated above the object to be controlled, the force feedback can be transmitted to the user only on the actuator 150, whereas a resistance below the object or an object part is merely transmitted to the actuator 152 and therefore leads to force feedback below the finger 106 of the user.

The actuator 154 shows an alternative embodiment. The former is arranged in the body 142 of the gripping element 14 in such a way that it surrounds the receptacle in the region of the finger 108, in particular at the distal end. Actuating this actuator 154 therefore leads to a uniform transmission of the force feedback to the finger 108. As a result, the transmission by such an actuator 154 can be clearer and hence also less ambiguous.

In order to achieve a corresponding actuation or operation of the actuators 150, 152 and 154, these have channels, as depicted in an exemplary manner by the channel 156 for the actuator 154. An appropriate fluid can flow into or out of the actuator 154 (or 150 and 152) through these channels. In so doing, the appropriate fluid is transmitted into the gripping element 14 through a channel 158 in the adapter element 28. In order also to be able to establish here a functional connection between the gripping element 14 and the adapter element 28, i.e., in particular between the receptacle element 132 and the connection element 146, a connection site 160 is also found on both elements between these two elements, i.e. between connection element 146 and receptacle element 132. The fluid can flow from the channel 158 into the channel 156 through this connection site 160 and hence into the actuator 154 or flow from the actuator 154 into the channel 158 through the channel 156. To this end, the connection site 160 can have different embodiments, for example in the form of two superposing openings, or else the form of a tubing plug, for example in the region of the gripping element 14, which engages into a tubing socket of the adapter element 28, or vice versa. If such actuators, which operate on the base of expansion, are to be provided in a corresponding adapter element (not depicted here), the adapter element may then also have an elastic design, at least in part.

In the shown actuators in the form of the cavities for the actuators 150 to 154, provision can also be made for the corresponding actuators to be embodied as (small) electric drives, for example vibration elements, electroactive polymers or other controllable elements, which ultimately lead to a change in shape and hence to an effect on a respective finger 106, 108 of a user.

In addition to the embodiment shown here, in which such a functional connection is established between the connection element 146 and the receptacle element 132 so that the communication to sensors 138 and 140 or from these, and to or from the actuators 150, 152 and 154 is made possible, it is also possible to provide for the corresponding connections for at least one or more of the above-described elements, i.e. sensors or actuators, being routed directly on the gripping element 14 to an element of the haptic input system or to the object to be controlled, or leading from the latter two into the gripping element 14. Furthermore, in addition to the embodiment shown here, in which the depicted lines, such as e.g. the channel 158, emerge from the adapter element 28, it is also feasible for these to be continued internally via a connector or an interface of the adapter element 28 to a haptic input system directly by means of installed lines or connections.

In a further embodiment, which is not shown again separately, a respective force-feedback element can also be embodied as a passive force-feedback element. As an example, reference is made here to the actuator 152, which can, for example, also be filled with an electrorheological (or else magnetorheological) liquid. This liquid can then be exposed to an electric field. By way of example, this can be realized by a feed line 162 in the adapter element 28. By applying an electric field to this electrorheological liquid in the actuator 152, the elasticity or the resistance against compression thereof changes. By way of example, this can be undertaken if an object to be controlled meets rather solid material during, for example, a gripping movement. The user then likewise feels this increased resistance, in the form of the electrorheological liquid of the actuator 152 being made less elastic, on his hand 66 by means of the finger 106.

Conversely, the electrorheological liquid in the actuator 152 can be made more elastic or provided with a lower resistance against compression by adapting the electric field by means of the feed line 162. By way of example, this would be appropriate if a corresponding object to be controlled meets rather softer material. In this case, the user would likewise experience this by means of his finger 106 as haptic feedback, i.e. as a type of force feedback. Since this feedback with these electrorheological liquids does not lead to a direct effect on the resting finger 106, as is the case e.g. in the above-described active force-feedback variants with electroactive polymers, fluid-filled cavities etc., this is referred to here, but not limited to, as passive force feedback within the scope of the present disclosure. In addition to the aforementioned variant with electrorheological liquids, magnetorheological liquids or other materials, which are able to change their elastic properties in a controlled manner, are accordingly also possible. In the case of magnetorheological liquids, the aforementioned changes occur as a result of a changeable magnetic field. This can likewise be controlled electrically by means of inductive effects.

FIG. 8 shows the simplified illustration of a further exemplary embodiment of a gripper input module 46 of one aspect. This gripper input module 46 likewise consists of a gripping element 16 and an adapter element 30, which is depicted in a simplified manner here. The gripping element 16 likewise has a receptacle 164, in which at least the fingers 106 and 108 of the hand 66 of a user can be held. Like in the examples shown above, this receptacle 164 is once again arranged in a body 166 of the gripping element 16. This body 166 also consists of an elastic material in the present example of the gripper input module 46. The gripping element 16 furthermore has a connection element 168, by means of which the gripping element 16 is connected to the adapter element 30. The adapter element 30 in turn has two paddles 170 and 172. The sides of the paddles 170 and 172, which face the fingers 106 and 108, come into contact with the gripping element 16 or the connection element 168 and hence form the receptacle element 174 of the adapter element 30. The paddles 170 and 172 are connected to one another, at least by means of a connection shaft 176. This connection shaft 176 is arranged in the adapter element 30 in such a way that it connects the paddles 170 and 172 to one another in a hinge-like fashion, wherein these can be pivoted with respect to one another about a central axis 178 of the connection shaft 176. This pivoting about the axis 178 leads to an angle setting 180 in accordance with the angle $\alpha$. This angle $\alpha$ specifies the angle of a corresponding paddle 170 or 172 in relation to corresponding longitudinal axis 182, which is comparable to the longitudinal axes through the adapter elements in the preceding exemplary embodiments. The angle between the paddles 170 and 172 can therefore be calculated by $2\times\alpha$. In an exemplary embodiment, the connection shaft 176 is embodied in such a way that it can detect an externally caused change in the angle 180 of the paddles 170 and 172. To this end, the connection shaft 176 may have an angle encoder (not shown).

This variant therefore likewise now provides a sensor means in the form of the connection shaft 176, which can likewise undertake a detection of the movement of the paddles 170 and 172. Here, this detection substantially occurs by virtue of there being a moving together of the paddles 170 and 172 about the axis 178, initiated by a gripping movement with the fingers 106 and 108 and made possible by the elastic embodiment of the body 166 of the gripping element 16. In other words, the angle $\alpha$ between a respective paddle 170 or 172 and the longitudinal axis 182 is reduced. In the same manner, an opening movement, in which the fingers 106 and 108 move apart, can also lead to the paddles 170 and 172 moving apart. The result is an increase in the respective angle 180 or $\alpha$, which can likewise be detected by the connection shaft 176. In order to be able to detect both pulling and compressive movements by the fingers 106 and 108 using the connection shaft 176, the gripping element 16 has a force-fit and may also have an interlocking and/or cohesive connection with the adapter element 30, i.e., in particular, this connection is between the connection element 168 and the receptacle element 174. By way of example, this can be realized by the provision of T-slots and corresponding tongues, as already described above. In addition, embodiments are also feasible, where corresponding secure connections are provided by pins, screws, rivets or the like. Moreover, the corresponding connection can also be realized by an adhesive connection between the receptacle element 174 and the connection element 168.

As a result of the gripping movement thus carried out and the corresponding yielding of the gripping element 16 or of the gripper input module 46, this embodiment of the gripper input module 46 is particularly ergonomic and very comfortable for a user in relation to operation.

Furthermore, the gripper input module 46 has a motor (not shown here) in a further exemplary embodiment. This motor is functionally connected to the connection shaft 176 and, for example, is arranged on or in the latter. As a result of this arrangement, the motor can control the pivoting of the paddles 170 and 172 about the axis 178. In other words, it is therefore possible to actuate the paddles 170 and 172 by means of the motor and to modify the angle between these. By actuating the motor, the gripper input module 46 therefore also has the option of returning force-feedback information or, in general, force feedback to a user. To this end, there can be active pulling-together of the fingers 106 and 108 in the present example, in addition to active pressure. Hence all effects that can act on an object to be controlled, such as e.g. a clamp, forceps or scissors, can also be transmitted onto this gripper input module 46. Here, the force feedback can have the form of an opening or closing pressure, as mentioned above, and also the transmission in the form of vibrations.

In addition to these active force-feedback variants by the motor, the latter can also have the properties of a passive force feedback already mentioned above. To this end, the motor can counteract or act with a corresponding movement by the fingers 106 and 108 of the user by means of an actuation on the connection shaft 176. The user thus receives the haptic impression on his hand 66 or on the fingers 106 and 108 as if he were, for example, to meet a very hard or a very soft object with the object to be controlled. In one explicit example, a cut through soft tissue with an instrument to be controlled can be promoted here, whereas, if cartilage or bone tissue is met, the resistance on the gripper input module 46 is increased. This is brought about accordingly by the opposite or promoting actuation of the motor in relation to a corresponding gripping movement.

FIG. 9 shows a further exemplary embodiment of a force-feedback system on the base of the gripping element 18. Here, the gripping element 18 likewise has a receptacle 184, in which at least the fingers 106 and 108 of the hand 66 of the user are held. Furthermore, arranged on the gripping element 18 is an actuator 186, by means of which a tactile element 188 can be actuated. To this end, provision is made for a force-fit or interlocking connection by means of rods 190. The tactile element 188 is arranged in the gripping element 18 in such a way that, as will still be described in more detail below, said tactile element can enter the receptacle 184 through small openings, directly through the gripping element 18, and therefore can come into contact with the finger 106 of the user.

The actuator 186 can then move the tactile element 188 toward the finger 106, i.e. upward in relation to the illustration of FIG. 9, by means of the rods 190, which are suspended on a shaft 192. This is indicated by an arrow 194. This upward movement in accordance with the arrow 194 can be embodied as a continuous, permanently pressing movement against the finger 106. Additionally, an exemplary embodiment is possible, in which the tactile element 188 is moved forward and backward against the finger 106, such that a vibration is created at the finger 106 by the tactile element 188. Here, the actuator 186 and the embodiment with the rods 190 can then be such that a corresponding forward and backward movement, i.e. in accordance with the arrow 194 and against it, is actively possible. Additionally, it is also feasible for only one movement direction in accordance with the arrow 194 (or the other direction) to be possible, while the opposite movement direction emerges due to pretension, for example by means of a spring.

Figure 10:
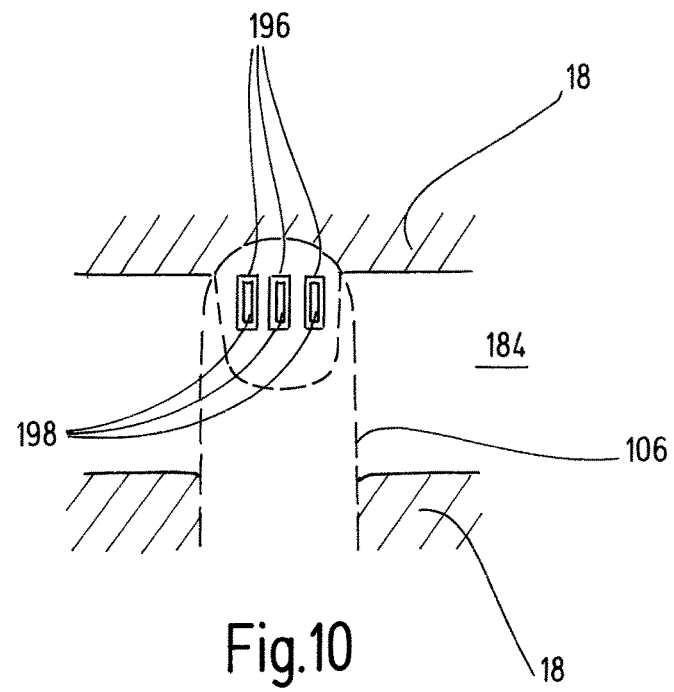
FIG. 10 shows a magnified sectional illustration of the active surface of the force-feedback system depicted in FIG. 9, in accordance with the line X-X from FIG. 9.

Here, FIG. 10 correspondingly shows a sectional view, with this being a top view of the tactile element 188. FIG. 10 therefore shows the gripping element 18 and the finger 106, the latter being depicted by dashed lines for reasons of clarity. Situated below the finger 106 are openings 196 in the gripping element 18 or in the receptacle 184. Lamellas 198, which are arranged proximally on the tactile element 188, can pass through these openings 196. This embodiment may therefore be, in particular, advantageous since a finger or the tactile sense thereof reacts very delicately and sensitively to vibrations. By way of example, this can be implemented by means of the arrangement with the lamellas 198 shown here, but also by other structures such as e.g. a dot matrix or else a planar embodiment.

In addition to an embodiment with openings 196, it is furthermore feasible only to have material weakening here such that vibration by the lamellas 198 can reach the finger 106, but the receptacle 184 is otherwise closed.

In the exemplary embodiments of the gripping elements 12 to 18 shown above, these may have an elastic design. Here elastic polymers in particular, such as e.g. silicone, which is preferably suitable for medical purposes, come into question. However, additionally, other embodiments with rigid or at least partially rigid bodies of the respective gripping elements are also within the scope of this invention. The exemplary gripping elements may furthermore be characterized by a self-supporting form, in which a hand 66 of the user can be held.

As already mentioned above in an exemplary manner, a corresponding gripping element can be embodied as a replaceable sheath or as a replaceable element. In this exemplary case, it may be preferable for the value and the material complexity and the production complexity connected with the respective gripping element to be kept as low as possible, in order to provide a hard-wearing disposable or reusable product here, which can be handled as easily as possible.

In addition to the shown exemplary embodiments, in which, in each case, a sensor is available in a direction of the respective fingers 106 and 108, it is naturally also feasible to enable an arrangement of a plurality of sensors next to one another, for example in the form of sensor arrays. As a result of this, it is possible, for example, to associate a corresponding sensor with each finger of a hand 66 and hence to capture the movement of each finger separately. In this manner, it is then also possible for either individual object elements of an object to be controlled to be actuated individually by the fingers or else for different fingers to be associated with different functions for an object to be controlled. In order to promote this arrangement, a corresponding exemplary gripping element may be provided with appropriate interruptions or other material changes between the corresponding fingers in a respective receptacle. As a result of this, it is possible to prevent pressure distributions which are created in the material of a corresponding gripping element by an actuation by means of a finger.

Alternatively, provision can be made for a corresponding gripping element with a common sensor element for recording the movement of one of the fingers present. What can thus be rendered possible is that, independently of the exact position of the fingers in a corresponding receptacle of a gripping element, i.e., for example, the rotational arrangement in relation to a longitudinal axis, a reliable actuation of the remote object to be controlled is always made possible. By way of example, this can be realized by virtue of the fact that a sensor is surrounded in the gripping element by material which ensures a corresponding force distribution. Thus, it is then possible, for example, to cause a same effect on the object to be controlled by the actuation with the little finger as by actuation with the index finger by virtue of a common sensor detecting this in the same manner due to the force distribution.

These aforementioned embodiments with sensor arrays, pressure or force distribution or restriction of this pressure or force distribution is analogously also possible using actuators for active or else passive force-feedback transmission.

The exemplary gripping elements 10 to 18 furthermore constitute an exemplary embodiment of one aspect, to the extent that they enclose the respective fingers of a hand in at least two directions, preferably from above and below. In addition to reliable operation of the haptic input system and improved ergonomics, this also enables the integration of the identification of pulling movements, that is to say opening movements of the fingers.

Figure 11:
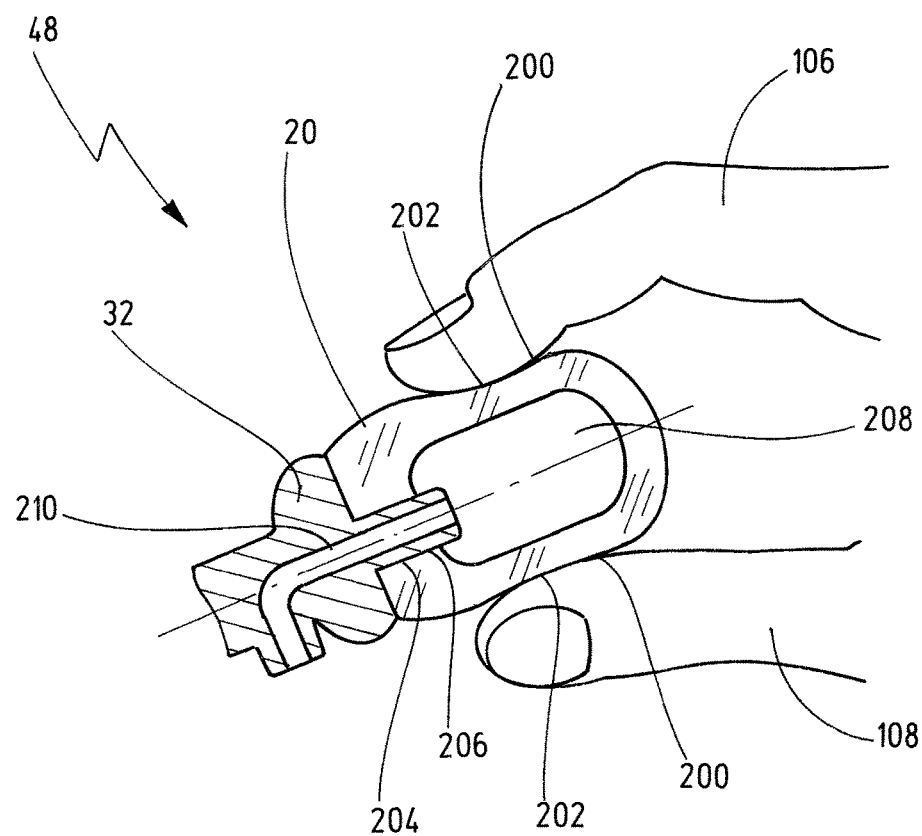
FIG. 11 shows a further exemplary embodiment of gripping element and adapter element in accordance with one aspect.

FIG. 11 shows a further exemplary embodiment of a gripper input module 48. This gripper input module 48 has a gripping element 20 and an adapter element 32. The adapter element 32 in turn has a receptacle element 204, which holds the gripping element 20 in a force-fit manner by means of a connection element 206 thereof. The gripping element 20 in turn has a receptacle 200 for holding fingers 106 and 108 of a user. In contrast to the preceding receptacles of the gripping elements 10 to 18 shown above, this receptacle 200 is not closed on the outer side of the fingers 106 and 108. For the purposes of securely holding the fingers 106 and 108, this gripping element 200 has an encircling depression 202.

A cavity 208 is furthermore provided in the interior of the gripping element 20. This cavity 208 can be filled with a fluid, such as e.g. a gas or a liquid, in order to expand the corresponding volume of the cavity 208. In the same manner, a corresponding fluid can be removed from this cavity 208 in order to compress the volume in the cavity 208. This exchange of fluids can take place by means of the adapter element 32. To this end, a channel 210 is provided in the adapter element 32. This channel 210 is connected to an external unit (not depicted in any more detail), which can bring about the corresponding fluid movement. Here, this can, for example, be a compressor or a pump, not shown in any more detail.

If a user now carries out a compression of the gripping element 20 by means of a gripping movement with the fingers 106 and 108, this ultimately leads to an increase in pressure in the cavity 208, which has a further effect over the channel 210. A sensor system not shown in any more detail here on the channel 210 can then detect this change in pressure. On the base of the detected pressure-change data, it is then possible to deduce the corresponding pressure force from the fingers 106 and 108. Subsequently, an actuation based thereon of an object to be controlled, such as e.g. closing scissors or a clamp, can be undertaken.

As a result of the above-described embodiment of the fluid transport through the channel 210 into the cavity 208, force feedback to the user, in particular to his fingers 106 and 108, can also be made possible thereby. To this end, the pressure or the volume in the cavity 208 is, for example, increased by the introduction of further fluid through the channel 210 if an object to be controlled meets a resistance. The user therefore obtains force feedback and hence information that a correspondingly more solid material or any other resistance for the object to be controlled is present. Conversely, the volume or the pressure in the cavity 208 can be reduced by the channel 210, by virtue of the fluid being removed from the cavity 208 in this manner. The user therefore then obtains force feedback so that there is no resistance or softer material in the region of the object to be controlled.

This force feedback can be undertaken as passive force feedback, by merely setting the appropriate pressure or volume in the cavity 208. In addition, however, the embodiment as active force feedback is also possible which, for example, also transmits active force feedback as vibration with varying compression and decompression processes of the cavity 208 in quick succession to the user by means of his fingers 106 and 108.

Since, in the example shown here, both the detection of the pressure exerted by the user and of the pressure, which is created by the increase of the fluid content in the cavity 208, are to be realized by one channel 210, provision is in this exemplary case may preferably be made for an appropriate feedback between the detection system and the fluid-feed system. As a result, it is possible to avoid read errors in the detection system, for example by a pressure sensor, which could otherwise occur as a result of the fact that an increase of the pressure with the goal of supplying force feedback ultimately leads to the system detecting a perceived movement of the fingers 106 and 108 by means of the pressure sensor.

In accordance with the explanations made above, the material of the gripping element 20 is also embodied as elastic material. Thus, the transmission of the pressure information from the fingers to the cavity 208 or from the cavity 208 to the fingers 106 and 108 can take place in a simple manner.

Figure 12:
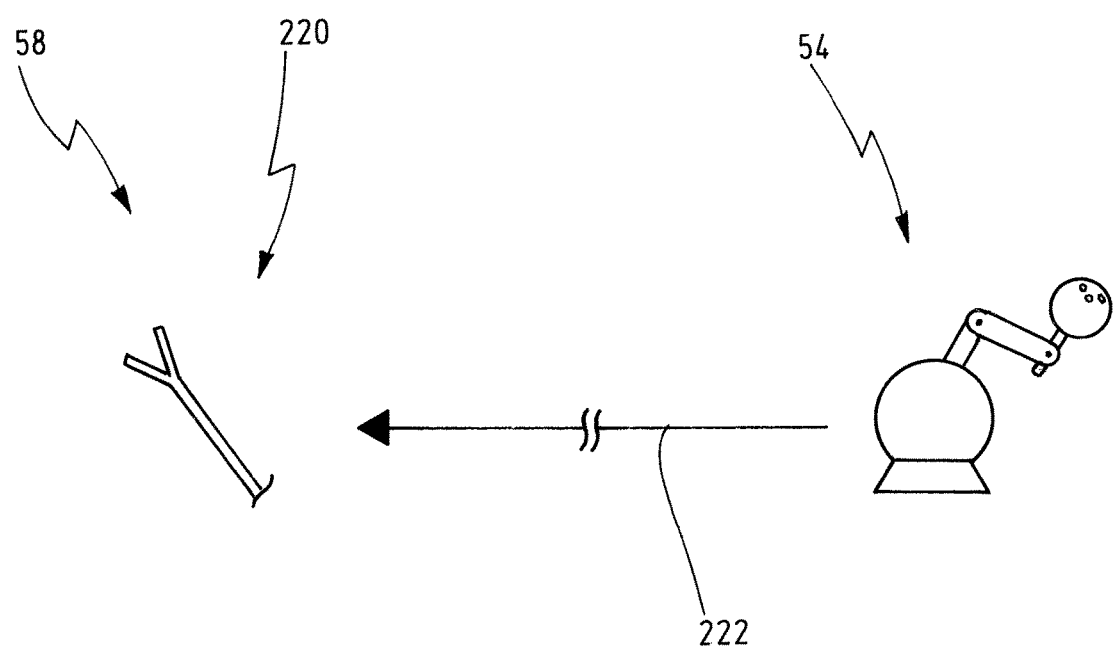
FIG. 12 shows a schematic illustration of a medical instrument system in accordance with one aspect.

FIG. 12 finally schematically shows the embodiment of the medical instrument system 58. This has an object 220 to be controlled, in the form of a cutting tool depicted here in a schematic manner. Opposite to this, the medical instrument system furthermore has a haptic input system, here e.g. the haptic input system 54. The haptic input system 54 has a functional connection to the object 220 to be controlled. This functional connection is indicated here in an exemplary manner by an arrow 222. As a result of this functional connection, the object 220 to be controlled can be controlled on the base of movements and operations on the haptic input system 54. In addition to controlling the object 220 to be controlled in the six degrees of freedom already mentioned above, i.e. in the three spatial directions and about three mutually orthogonal axes of rotation, the haptic input system 54 can have a gripper input module embodied in accordance with the explanations made above. This renders it possible to actuate the object 220 to be controlled. By way of example, this can be a cutting process in the example shown here of the object 220 to be controlled in the form of a cutting tool. This cutting process can be triggered by a gripping movement of the fingers 106 and 108 in the gripper input module, i.e., in particular, in the respective gripping element. Conversely, an opening movement can lead to an opening of the object 220 to be controlled in the form of the cutting tool shown here.

The functional connection 222 described here can be brought about either by electrical signals or else by electromagnetic signals. Hence, in addition to conventional connections by cables or other fixed connections, this also includes wireless transmissions. To this end, object 220 to be controlled and haptic input system 54 can be in a room or in a building. Furthermore, an arrangement is also feasible, in which the functional connection 222 is possible over relatively large distances.

If the haptic input system 54 is applied at the same location as the object 220 to be controlled, the sterility and hygiene of the haptic input system 54 should be noted in the exemplary case of use in a surgical intervention. By way of example, to this end, the equipment itself can be provided with a protective sheath, while a corresponding gripping element, which comes into direct contact with the operating surgeon by means of his hand 66, can, in accordance with one aspect, be embodied as product that can easily be sterilized or as disposable product.

In relation to the illustration of FIG. 5, one aspect relates to a gripping element 10 for arrangement on an adapter element 24 in order to form a gripper input module 40 for a haptic input system for controlling at least one object, comprising at least one receptacle 68 for holding at least two fingers 106, 108 of a user therein, wherein, at least in one portion, the receptacle has a functional connection to at least one sensor means 110, and at least one connection element 90 for arranging the gripping element 10 on the adapter element 24, wherein the receptacle 68 is configured such that movement information of a movement of at least one finger 106, 108 of the user in the receptacle 68 can be detected by the sensor means 110 and hence the movement information can be transmitted for controlling the at least one object. One aspect furthermore relates to a corresponding adapter element 24, a gripper input module 40 consisting of a gripping element 10 and adapter element 24, as well as to a haptic input system and medical instrument system.

What is claimed is:

1. A gripping element configured to be arranged on an adapter element in order to form a gripper input module of a haptic input system configured to control at least one object, the gripping element comprising:
    at least one receptacle configured to hold at least two fingers of a user therein, wherein, at least in one portion, the at least one receptacle has a functional connection to at least one sensor; and
    at least one connection element configured to arrange the gripping element on the adapter element;
    wherein the at least one receptacle is configured such that movement information of a movement of at least one finger of the user in the at least one receptacle is detected by the sensor, and hence the movement information is transmitted to control the at least one object.

2. The gripping element of claim 1, wherein the gripping element is substantially produced from an elastic material.

3. The gripping element of claim 1, wherein the functional connection to the at least one sensor is realized by an elastic material.

4. The gripping element of claim 1, wherein the at least one receptacle is configured such that a movement of at least one finger of the user in the at least one receptacle can, by the connection element, be detected by at least one sensor, which is arranged on the adapter element.

5. The gripping element of claim 1, wherein the gripping element has at least one sensor configured to detect at least one movement of at least one finger of the user in the at least one receptacle.

6. The gripping element of claim 5, wherein the at least one sensor has at least one sensor comprising at least one of a pressure sensor, a force sensor and a movement sensor.

7. The gripping element of claim 1, wherein the at least one receptacle is furthermore configured such that it enables a transmission of at least one item of force-feedback information to at least one finger, which is held in the at least one receptacle, of the user.

8. The gripping element of claim 7, wherein the at least one receptacle is configured such that the at least one item of force-feedback information can, by the connection element, be transmitted from the adapter element to at least one finger, which is held in the at least one receptacle, of the user.

9. The gripping element of claim 1, wherein the gripping element has at least one actuator, by which at least one item of force-feedback information is transmitted to at least one finger, which is held in the at least one receptacle, of the user.

10. The gripping element of claim 1, wherein the gripping element has at least one passive force-feedback element.

11. An adapter element configured to detachably hold a gripping element, in order to form a gripper input module of a haptic input system configured to control at least one object, the adapter element comprising:
    an interface configured to communicate with the haptic input system or the at least one object; and
    at least one receptacle element configured to hold the gripping element on the adapter element;
    wherein the at least one receptacle element is configured such that the adapter element and a gripping element connectable thereto is brought into functional connection by a sensor configured to detect movement information of at least one finger of the user in a receptacle of the gripping element.

12. The adapter element of claim 11, wherein the adapter element has at least one sensor configured to detect at least one movement of at least one finger of the user.

13. The adapter element of claim 12, wherein the at least one sensor has at least one sensor comprising at least one of a pressure sensor, a force sensor and a movement sensor.

14. The adapter element of claim 11, wherein the at least one receptacle element is configured such that at least one item of force-feedback information can, by the gripping element, be transmitted to at least one finger of the user, which is held in a receptacle of the gripping element.

15. The adapter element of claim 11, wherein the adapter element has at least one actuator, by which at least one item of force-feedback information is transmitted to at least one finger of the user, which is held in a receptacle of the gripping element.

16. The adapter element of claim 11, wherein the adapter element has at least one passive force-feedback element.

17. A gripper input module, comprising:
    a gripping element of claim 1;
    an adapter element configured to hold the gripping element for operating a haptic input system configured to control at least one object, wherein the adapter element has an interface configured to communicate with the haptic input system or the at least one object; and
    at least one receptacle element configured to hold the gripping element on the adapter element;
    wherein the gripping element and/or the adapter element has a functional connection to at least one sensor.

18. The gripper input module of claim 17, wherein the adapter element is an adapter element of claim 11.

19. A haptic input system configured to control at least one object, comprising an adapter element of claim 11.

20. A haptic input system configured to control at least one object, comprising a gripper input module of claim 17.

21. A medical instrument system, comprising:
    at least one medical instrument; and
    at least one haptic input system of claim 19;
    wherein the at least one medical instrument is configured to be controlled by the haptic input system.

* * * * *